(12) United States Patent
Lian et al.

(10) Patent No.: US 9,026,198 B2
(45) Date of Patent: May 5, 2015

(54) METHOD AND DEVICE FOR NOISE DETECTION IN PHYSIOLOGICAL SIGNALS

(75) Inventors: Jie Lian, Beaverton, OR (US); Dirk Muessig, West Linn, OR (US)

(73) Assignee: Biotronik SE & Co. KG (DE)

( * ) Notice: Subject to any disclaimer, the term of this patent is extended or adjusted under 35 U.S.C. 154(b) by 6 days.

(21) Appl. No.: 13/155,690

(22) Filed: Jun. 8, 2011

(65) Prior Publication Data

US 2012/0016249 A1 Jan. 19, 2012

Related U.S. Application Data

(60) Provisional application No. 61/363,669, filed on Jul. 13, 2010, provisional application No. 61/468,074, filed on Mar. 28, 2011.

(51) Int. Cl.
*A61B 5/04* (2006.01)
*A61B 5/0452* (2006.01)
*A61B 5/00* (2006.01)

(52) U.S. Cl.
CPC ............ *A61B 5/0452* (2013.01); *A61B 5/7221* (2013.01); *Y10S 128/901* (2013.01)

(58) Field of Classification Search
CPC .. A61B 5/7221; A61B 5/0452; A61B 5/7203; A61B 5/7207
USPC ........... 607/509, 521; 128/901, 902; 600/509, 600/521
See application file for complete search history.

(56) References Cited

U.S. PATENT DOCUMENTS

| | | | |
|---|---|---|---|
| 5,647,379 A | 7/1997 | Meltzer | |
| 5,891,048 A | 4/1999 | Nigam et al. | |
| 5,999,845 A | 12/1999 | dePinto | |
| 6,230,059 B1 | 5/2001 | Duffin | |
| 6,321,115 B1 * | 11/2001 | Mouchawar et al. | 607/9 |
| 6,345,199 B1 | 2/2002 | Thong | |
| 6,470,215 B1 | 10/2002 | Kraus et al. | |
| 6,574,509 B1 | 6/2003 | Kraus et al. | |
| 6,622,043 B1 | 9/2003 | Kraus et al. | |
| 6,917,830 B2 | 7/2005 | Palreddy et al. | |
| 7,027,858 B2 | 4/2006 | Cao et al. | |
| 7,467,009 B2 | 12/2008 | Palreddy et al. | |
| 7,474,247 B1 | 1/2009 | Heinks et al. | |
| 7,496,409 B2 | 2/2009 | Greenhut et al. | |
| 7,570,989 B2 | 8/2009 | Baura et al. | |

(Continued)

FOREIGN PATENT DOCUMENTS

WO    WO 2008/134422 A2    11/2008

OTHER PUBLICATIONS

European Search Report of Nov. 21, 2011 for parallel EP Appln. 11172371.

*Primary Examiner* — Michael Kahelin
*Assistant Examiner* — Mallika D Fairchild
(74) *Attorney, Agent, or Firm* — Craig A. Fieschko, Esq.; DeWitt Ross & Stevens S.C.

(57) ABSTRACT

A method for determining the signal quality of samples in a physiological signal, in particular an electrocardiogram (ECG) signal, is provided. A supra-threshold sample sum, a noise threshold crossing sum, or both are calculated in a noise detection window including the sample to be evaluated, and low signal quality is indicated if either or both of the sums exceed respective values. ECG beat detections can then be labeled as unreliable based on the determination of low signal quality for one or more samples between the detections.

25 Claims, 14 Drawing Sheets

(56) References Cited

U.S. PATENT DOCUMENTS

| | | |
|---|---|---|
| 2004/0049120 A1 | 3/2004 | Cao et al. |
| 2007/0255150 A1 | 11/2007 | Brodnick |
| 2008/0161873 A1 | 7/2008 | Gunderson |
| 2008/0269813 A1 | 10/2008 | Greenhut et al. |
| 2008/0300497 A1 | 12/2008 | Krause et al. |
| 2010/0312131 A1 | 12/2010 | Naware et al. |

* cited by examiner

METHOD AND DEVICE FOR NOISE DETECTION IN PHYSIOLOGICAL SIGNALS

CROSS-REFERENCE TO RELATED APPLICATIONS

This application claims priority under 35 USC §119(e) to U.S. Provisional Patent Application 61/363,669 filed Jul. 13, 2010, and to U.S. Provisional Patent Application 61/468,074 filed Mar. 28, 2011. The entireties of these prior applications are incorporated by reference herein.

TECHNICAL FIELD

The present invention generally relates to medical devices that measure and analyze the cardiac electrical signals. More particularly, the present invention relates to a method and device for quantifying signal quality from electrocardiogram (ECG) signals, including surface electrocardiogram, subcutaneous electrocardiogram, and intracardiac electrogram signals. The invention further relates to medical devices for processing sampled physiological signals, and in particular to devices having means for sensing the foregoing types of signals, and also having a processor adapted to determine the quality of the signal(s).

BACKGROUND

Regardless of the type of device used to record ECG signals (e.g., ECG machines, bedside ECG monitors, Holter ECG monitors, subcutaneous ECG devices, implantable cardiac pacemakers, etc.), reliable beat detection is needed for further ECG processing and clinical diagnosis. Beat detection may involve the detection of signal peaks that exceed a preset threshold and that presumably represent heart contractions. However, the accuracy of ECG beat detection is often compromised by noise from many different sources, such as high frequency muscle noise and electromagnetic interference (EMI), low frequency noise due to respiration, saturation noise due to charge overloading of sense amplifiers, and so on. Advanced filter design can reduce, but not eliminate, these noises.

Noise in an ECG signal can cause two types of beat detection errors. A false positive (FP) occurs when a beat detection algorithm falsely generates a sense marker (i.e., an indication of a beat) when there is no QRS complex, and a false negative (FN) occurs when a beat detection algorithm fails to detect the true QRS complex. Although it is well known that large noise can cause FPs and small signal can lead to FNs, it is important to realize that FPs can also occur at low noise levels and FNs can also occur when signal amplitude is high. For example, many ECG beat detection algorithms automatically apply a blanking window after each beat detection and then dynamically adjust the sensing threshold (with an example of an auto-sensing algorithm being disclosed in U.S. Pat. No. 5,891,048). When the sensing threshold becomes too low, a sample with small noise amplitude may trigger a false detection (i.e. FP). On the other hand, each false detection may trigger a blanking window during which a true QRS may be missed from detection (i.e., an FN can result). Therefore, for reliable ECG beat detection, a high signal-to-noise ratio (SNR) is desired. In other words, when SNR is low, ECG beat detections may be unreliable.

Both FPs and FNs can cause problems for ECG rhythm analysis. For example, FPs and FNs can lead to irregular RR intervals, which could be misinterpreted by a medical device as atrial fibrillation. As another example, frequent FPs may lead to very short RR intervals, which could be misdiagnosed by the device as ventricular tachyarrhythmia. As yet another example, consecutive FNs may generate very long RR intervals, which could be misdiagnosed by the device as bradycardia or ventricular asystole. As a result, physicians may have to spend significant time and effort to examine these false rhythm classifications. Moreover, for ECG loop recorders, these false rhythm alarms could overwhelm the device's memory, which otherwise could have been used to store more useful arrhythmic episodes.

In U.S. Pat. No. 7,496,409 to Greenhut et al, the signal quality of a subcutaneous ECG is measured by several metrics, including R wave amplitude, a signal-to-noise ratio such as an R-wave peak amplitude to a maximum or average waveform amplitude between R-waves or an R-wave to T-wave amplitude ratio, a signal slope or slew rate, a low slope content, a relative high versus low frequency power, mean frequency or spectral width estimation, probability density function, normalized mean rectified amplitude, or any combination of these metrics. These metrics require high computation power and are not suitable for implementation in implantable devices, and/or have unsatisfactory performance to characterize the noise conditions.

In U.S. Pat. No. 6,230,059 to Duffin, each stored data episode is checked for noise conditions. Specifically, the most frequently occurring amplitude value (MCV) in the data set is determined, and a baseline amplitude value or range is derived from the MCV. The crossings of the baseline value are determined, and a crossing count of the total number of crossings of the baseline value is made. The crossing count is compared to a noise threshold count, and the ECG episode data is tagged as noisy if the crossing count exceeds or equals the noise threshold count, or is tagged as noise free if the noise threshold count is less than the crossing count. There are several major limitations of this method. First, it can only be applied to a data episode, and cannot be used for noise detection on a beat-by-beat basis. Second, the MCV is affected by the episode. When the episode is not representative of the quiescent ECG segments, the MCV may deviate from the true baseline. Third, the baseline range is arbitrarily defined without consideration of the signal amplitude. As a result, an ECG episode may be tagged as noisy despite its large signal-to-noise ratio (SNR), whereas another ECG episode may be tagged as noise-free despite its small SNR.

In U.S. Pat. No. 7,467,009 and U.S. Pat. No. 6,917,830 to Palreddy et al, the presence or absence of noise is determined by computing the density of local peaks or inflection points in the ECG waveform. A sample is defined as the inflection point if its amplitude is greater, or smaller, than both its preceding and the following samples by predefined threshold values. Because the predefined threshold values are not adaptive to the signal amplitude, more inflection points may be detected for an ECG signal with high SNR than another ECG signal with small SNR.

U.S. Pat. No. 7,474,247 to Hinks et al. describes a method to detect saturation noise by means of an integrator or quantizer in the front-end circuit, but does not address the more challenging task of detecting high-frequency noise introduced by muscle activities or EMI.

In U.S. Pat. No. 7,027,858 to Cao et al., the noise markers are generated if the detection intervals are considered as too short to be physiologically valid. A similar concept is also described in U.S. Pat. Appl. 2008/0161873 to Gunderson, and in U.S. Pat. Appl. No. 2008/0300497 to Krause et al. These interval-based noise detection methods are neither sensitive nor specific for noise detection.

U.S. Pat. No. 7,570,989 to Baura et al. describes a method which uses the change in RR interval from the previous beat, and the change in mean squared error (MSE) from the last n (e.g. n=2) good beats, to determine whether the beat under analysis should be further processed. The MSE change and the RR interval change could be caused by many factors other than noise, so this method is not reliable for noise detection.

U.S. Pat. No. 5,999,845 to dePinto describes a method to detect wideband noise by measuring the running average of the squared sample values of the ECG signal with QRS complex blanked.

U.S. Pat. No. 5,647,379 to Meltzer describes a method to detect the level of EMI component of an input biomedical signal by calculating a correlation function. However, none of these methods has proven accuracy in quantifying the ECG signal quality.

US Pat. Appl. Pub. 2010/0312131 A1 to Naware et al. describes a method for noise detection by counting the number of noise threshold crossings in a noise detection window, where the noise threshold is preferably a specified percentage of the beat detection sensing threshold. This method has several shortcomings. First, the beat detection sensing threshold may or may not be adaptive to the signal amplitude. As a result, there is no guarantee that the noise threshold reflects the signal amplitude, and thus the method does not take into account the signal to noise ratio in noise detection. Second, the noise window is either fixed or back-to-back, and thus the method does not allow sample-by-sample or real-time noise detection. Third, the noise detection window is triggered by sensed ventricular events. Therefore, under-sensing of ventricular events will not trigger noise detection, thereby leading to under-detection of noises. On the other hand, over-sensing of large artefacts may lead to too high of a noise threshold, which can also lead to under-detection of noises.

SUMMARY

In view of the foregoing systems, there is a need for methods and devices having more reliable detection of noise in physiological signals, so that noisy beats and intervals are excluded from the rate and rhythm analysis. There is also a need for an implantable device having a processor which implements a method for more reliable noise detection.

A preferred version of the invention involves a method for determination of a noise in a sampled physiological signal, wherein the sampled physiological signal includes a consecutive sequence of samples, each sample having an amplitude, the amplitudes in general being positive or negative, with the method including the steps of:
  providing a signal quality check window (denoted herein as QCW, but also referred to a noise detection window) that includes a number of consecutive samples (NZDW);
  providing at least one upper threshold for a signal amplitude (the upper threshold being denoted herein as NZTHRESH, or where multiple thresholds are used, as HITHRESH and LOTHRESH);
  providing at least one lower threshold for a signal amplitude (the lower threshold being denoted herein as −NZTHRESH, or where multiple lower thresholds are used, as −HITHRESH and −LOTHRESH), wherein each of the upper threshold(s) and the lower threshold(s) define at least three amplitude ranges, a high range for signal amplitudes exceeding the upper threshold, a medium range for amplitudes between the upper threshold and the lower threshold, and a low range for amplitudes below the lower threshold;
  comparing each sample within the quality check window QCW (noise detection window) with the upper threshold and with the lower threshold; and
  performing a signal quality analysis for the signal sample by analyzing the changes in amplitude of successive samples within the quality check (noise detection) window QCW, the change in amplitude being determined for any two adjacent sample pairs within the window QCW by comparing to which amplitude ranges the amplitudes of the signal samples of the respective sample pair belong to.

The method preferably further includes determining a threshold crossing count (i.e., the number of noise threshold crossings, denoted herein as NZX_CNT) reflecting the number of thresholds between each two adjacent signal samples of each sample pair.

The method preferably further includes determining a noise threshold crossing sum (NZX_SUM) of the threshold crossing counts NZX_CNT for a respective quality check (noise detection) window QCW containing NZDW samples. In a preferred version, the noise threshold crossing sum NZX_ SUM is preferably a weighted sum with predetermined weights for each threshold crossing count magnitude.

The noise condition is preferably continuously evaluated on a sample-by-sample basis, e.g. by moving the noise detection window. The amplitudes of the samples can be either positive or negative, but the invention can also be applied for signals either having only positive or only negative values. In the latter case, providing only one noise threshold may be sufficient.

Parameters such as the number of samples NZDW contained in a respective quality check (noise detection) window QCW; the upper threshold(s) (NZTHRESH, or HITHRESH and LOTHRESH); and/or the lower threshold(s) (−NZTHRESH, or −HITHRESH and −LOTHRESH), can either be fixed or can be updated during operation. Each sample is associated with the quality check or noise detection window QCW that has the length of the sample number NZDW.

The physiological signal is preferably an electrocardiogram (ECG) signal, e.g., a surface electrocardiogram signal or a subcutaneous electrocardiogram signal, or an intracardiac electrogram signal. The physiological signal can also refer an impedance signal, a transthoracic impedance signal, an intracardiac impedance signal, or any other electrical signal reflecting cardiac activity.

The magnitudes and senses (positive/negative) of the upper noise threshold (NZTHRESH, or HITHRESH and LOTHRESH) and the lower noise threshold (−NZTHRESH, or −HITHRESH and −LOTHRESH) can vary. Preferably, if the ECG signal has a mean value of almost zero, the upper noise threshold is positive and the lower noise threshold is negative, and the magnitudes of NZTHRESH and −NZTHRESH (or HITHRESH and −HITHRESH, and LOTHRESH and −LOTHRESH) are identical.

In order to detect beats and/or QRS complexes, an ECG beat detection can be performed by determining if an amplitude of any sample exceeds a beat detection threshold, and generating a sense marker (beat indication) for this sample. The value of the beat detection threshold can be predefined and is either fixed or continuously updated during operation. Preferably, a peak detection window (denoted herein as PKDW) is defined around the sense marker, having predefined length and position with respect to the sense marker. A maximum absolute amplitude of all samples in the peak detection window PKDW is then determined as a peak value (denoted herein as PEAK). This yields an indication for the peak value of a QRS complex.

In a preferred version, the upper noise threshold (e.g., NZTHRESH) and/or the lower noise threshold (e.g., −NZTHRESH) are recalculated after each ECG beat detection. This allows for an adaptation of the thresholds to ambient conditions that could change with time.

The noise threshold (e.g., NZTHRESH) can be kept constant until the next beat detection, or can be lowered to a predefined minimum noise threshold (e.g., a value MIN_NZTHRESH) when no beat is detected after a predefined duration.

Preferably, the one upper noise threshold (NZTHRESH) is recalculated after an ECG beat detection, each ECG beat detection yielding a peak value PEAK corresponding to a maximum absolute amplitude measured during a peak detection window PKDW, by performing the following steps:

(a) calculating a minimum value (denoted herein as NEW_PEAK) by taking the minimum of a peak value PEAK of a recently performed ECG beat detection, and a weighted average value (denoted herein as OLD_PEAK) calculated directly after the previous ECG beat detection and being scaled by a first predefined scaling factor (denoted herein as p) larger than one, (b) calculating a weighted average value OLD_PEAK of the minimum value NEW_PEAK calculated in step (a), and the weighted average value OLD_PEAK calculated directly after the previous ECG beat detection, wherein the minimum value NEW_PEAK and the weighted average value OLD_PEAK are each weighted by respective predefined weighting factors (denoted herein as w1, w2), the predefined weighting factors w1, w2 summing to one, and (c) recalculating the at least one upper noise threshold (e.g., NZTHRESH) by taking the maximum of either a predefined minimum threshold value (denoted herein as MIN_NZTHRESH), or the weighted average value OLD_PEAK calculated in step (b) and being scaled by a second predefined scaling factor (denoted as f), the second predefined scaling factor (f) being larger than zero and smaller than one.

With these steps, the upper noise threshold (e.g., NZTHRESH) does not fall below the minimum threshold value (MIN_NZTHRESH) to avoid having too many samples being erroneously qualified as noisy. It further provides for a smooth adaptation to changing peak PEAK values, i.e. a sudden change in the peak value PEAK does not lead to an immediate change of the upper noise threshold by the same order of magnitude. This is advantageous if a single peak has an unnaturally high value due to certain adverse effects.

The lower threshold can be adapted accordingly, e.g., it can be set to the negative of the upper threshold.

Noise detection is preferably performed by:
providing a sample number (e.g., NZDW), an upper noise threshold (e.g., NZTHRESH) and a lower noise threshold (e.g., −NZTHRESH),
defining a noise detection window including a number NZDW of samples including a last sample (denoted herein as k), the number corresponding to the sample number,
determining a supra-threshold sample sum (denoted herein as STS_SUM) corresponding to the number of samples in the noise detection window NZDW that have an amplitude that either exceeds the upper noise threshold NZTHRESH or falls below the lower noise threshold −NZTHRESH, respectively,
determining a noise threshold crossing sum (denoted herein as NZX_SUM) corresponding to the sum of the number of noise threshold crossings between each two consecutive samples in the noise detection window,
indicating a noise condition for each last sample (k) of each noise detection window, if
the noise threshold crossing sum NZX_SUM exceeds a first predefined value (denoted herein as TX1), or
the supra-threshold sample sum STS_SUM exceeds a second predefined value (denoted herein as ST1), or
the noise threshold crossing sum NZX_SUM exceeds a third predefined value (denoted herein as TX2) and the supra-threshold sample sum STS_SUM exceeds a fourth predefined value (denoted herein as ST2).

The noise threshold crossing sum NZX_SUM is a measure for the occurrences of crossings of the upper noise threshold NZTHRESH and the lower noise threshold −NZTHRESH in between each two consecutive samples. If the amplitudes of two consecutive samples in the noise detection window both exceed the upper noise threshold NZTHRESH, or both lie between the upper noise threshold NZTHRESH and the lower noise threshold −NZTHRESH, or both fall below the lower noise threshold −NZTHRESH, the noise threshold crossing sum NZX_SUM remains unchanged. If the amplitude of one of two consecutive samples exceeds the upper noise threshold NZTHRESH and the amplitude of the other one lies between the upper noise threshold NZTHRESH and the lower noise threshold −NZTHRESH, the noise threshold crossing sum NZX_SUM is increased by one. If the amplitude of one of two consecutive samples falls below the lower noise threshold −NZTHRESH and the amplitude of the other one lies between the upper noise threshold NZTHRESH and the lower noise threshold −NZTHRESH, the noise threshold crossing sum NZX_SUM is also increased by one. If the amplitude of one of two consecutive samples exceeds the upper noise threshold NZTHRESH and the amplitude of the other one falls below the lower noise threshold −NZTHRESH, the noise threshold crossing sum NZX_SUM is increased by two. Thus, the noise threshold crossing sum NZX_SUM indicates how often the first threshold NZTHRESH or the second threshold −NZTHRESH, respectively, fall between amplitudes of consecutive samples in the noise detection window.

A noise condition (i.e., low signal quality indication) is indicated for the last sample (k) of each noise detection window if either the noise threshold crossing sum NZX_SUM exceeds a first predefined value (TX1), or the supra-threshold sample sum STS_SUM exceeds a second predefined value (ST1), or the noise threshold crossing sum NZX_SUM exceeds a third predefined value (TX2) and the supra-threshold sample sum STS_SUM exceeds a fourth predefined value (ST2). Thus, the method provides for a simple and reliable detection of the noise condition for each sample (k) out of a sequence of samples.

For calculating the supra-threshold sample sum STS_SUM, each sample in the noise detection window NZDW is evaluated in terms of its amplitude. If the amplitude lies between the upper noise threshold NZTHRESH and the lower noise threshold −NZTHRESH, the supra-threshold sample sum STS_SUM remains unchanged. If the amplitude either exceeds the upper noise threshold NZTHRESH or falls below the lower noise threshold −NZTHRESH, the suprathreshold sample sum STS_SUM is increased by one.

Determining the noise condition for the last sample of the noise detection window NZDW allows determination of the noise condition in real time for each new sample on a moving window basis. This is because each noise detection window NZDW includes a new sample and the NZDW-1 samples immediately preceding the new sample. As a consequence, the method allows for real time noise detection for each new sample.

In a preferred version of the invention, when a low signal quality (i.e., a noise condition) is indicated for any given sample, the detected beats immediately before and immediately after this sample are labeled as unreliable. The intervals associated with this pair of unreliable detections can be labeled as a noisy interval. In another version, signal quality (noise detection) is evaluated on a moving window basis. The moving window consists of a predefined number Y of samples. When a low signal quality (a noise condition) is indicated for another predefined number X out of Y samples, the noise condition is confirmed. Then the detected beats immediately before and immediately after this window are labeled as unreliable. The intervals associated with this pair of unreliable detections can be labeled as a noisy interval.

A weighted noise threshold crossing sum (weighted NZX_SUM), also referred to herein as a complexity index (denoted herein as CI), can also be calculated. The complexity index can be compared with a predefined complexity index threshold, and an indication of low signal quality can be issued if the complexity index exceeds the complexity index threshold.

The invention also encompasses a medical device for processing a sampled physiological signal. Preferably, the medical device is an implantable device having an electrocardiogram (ECG) signal sensor and a processor, wherein the processor is configured to determine a noise condition of one or more samples of an electrocardiogram (ECG) signal by performing the noise determination method described previously (and doing so with an ECG signal sensed by the device). The medical device may additionally or alternatively perform the other methods described above.

Further details of the invention can be understood from the following text and accompanying drawings.

DETAILED DESCRIPTION OF PREFERRED VERSIONS OF THE INVENTION

Figure 1:
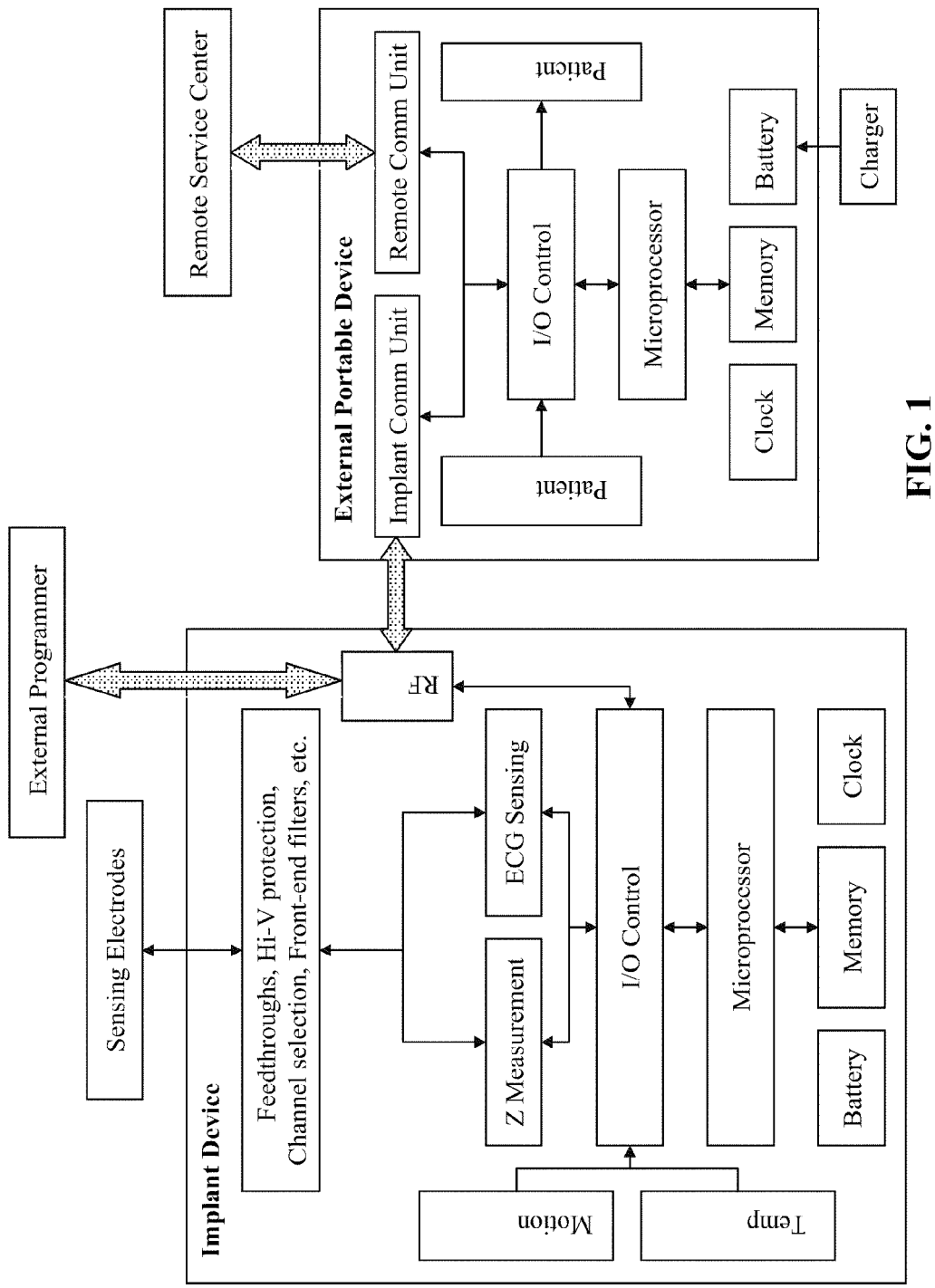
FIG. 1 shows a block diagram of an exemplary implantable subcutaneous ECG monitoring device, and its interfaces with an external portable device which further communicates with a remote service center, and with an external programming device.

FIG. 1 shows a block diagram of an implantable device for subcutaneous ECG monitoring, its (optional) interfaces with a (local or remote) external programmer for wired or wireless reprogramming of the device, and an (optional) external portable device, which may further communicate with a remote service center. The implantable device includes electronic circuitry that is hermetically sealed inside a casing (also known as a "can"), which is made from a biocompatible conductive material such as titanium. The device preferably includes a non-conductive header attached to the can, and sensing electrodes (preferably three or more), with or without leads connected to the header.

The sensing electrodes, which are electrically isolated from one another, may be mounted upon the outer surface of the can, or outside the header (if available), or at the distal ends of the leads (if available). For subcutaneous ECG recording, one or more pairs of sensing electrodes form the sensing vectors and the inter-electrode distance is preferably greater than 3 cm.

The leads are optional for subcutaneous ECG recording. If the measured subcutaneous ECG amplitude is too small for reliable sensing despite configuring different sensing vectors and recording at different anatomical locations, then one or more subcutaneous leads (with distal electrodes) could be tunneled under the patient's skin and connected to the header. A larger subcutaneous ECG amplitude can then be measured by increasing the inter-electrode distance, e.g., between the lead electrode and the can or header electrode.

A microprocessor and associated circuitry enclosed inside the hermetically sealed can make up the controller of the implant device. The implant device is powered by a battery, and maintains an internal clock for timing the operations. The microprocessor communicates with a memory via a bi-directional data bus. The memory typically includes a ROM or RAM for program storage and a RAM for data storage.

The sensing electrodes are first connected to an electronic interface that preferably includes a feedthrough circuit for noise reduction, a high voltage protection circuit, a switch network circuit for sensing channel selection, and front-end analog filters, such components being well known in the field. The configurations of the interface circuits (e.g., filter settings, sensing channel selection, etc.) can be programmed by the microprocessor.

The microprocessor connects to an I/O control unit to manage the input and output of the implant device. One input signal is the subcutaneous ECG picked up by the sensing electrodes. After being pre-processed by the interface circuitry, the subcutaneous ECG signal is further processed by the ECG sensing unit, which usually includes amplifiers, analog-to-digital converters, digital filters, etc., as known in the field. The physiological signal is sampled by way of the analog to digital conversion.

Another input signal is the impedance (Z) signal measured between the sensing electrodes. By injecting a small constant current (e.g., 100 µA, preferably biphasic) between two electrodes while measuring the voltage difference between the same or different pair of electrodes, the impedance is calculated as the ratio between the measured voltage difference and the injected current strength. As known in the field, the impedance signal provides useful information on the integrity of the sensing channel. In addition, the continuously measured impedance signal may be further processed by the microprocessor to extract other data regarding the physiological status of the patient, such as the respiration rate.

Other types of physiological signals measured by specific sensors can also serve as inputs to the implant device. For example, an on-board accelerometer can serve as a motion sensor that provides a patient activity signal to the implant device, and an on-board (or embedded in a lead) temperature sensor can provide a subcutaneous temperature signal to the implant device. Other types of input signals include, but are not limited to, a subcutaneous pressure signal measured by a pressure sensor, an acoustic signal measured by an acoustic sensor, a subcutaneous pH signal measured by a pH sensor, etc.

By running the program stored in the memory, the microprocessor also sends instructions to the ECG sensing unit, the impedance measurement unit, and other input measurement units to control how these signals are acquired (e.g., gain, offset, filter settings, sampling frequency, sampling resolution, etc.).

The acquired physiological signals are then stored in the device memory according to predefined storage modes. One typical mode is the queue-loop mode, meaning the acquired signals are stored in a predefined memory space, and when the allocated memory space is full, the newly acquired signals replace the oldest stored data (typically in first-in, first-out fashion). Another typical mode is the snapshot mode, meaning the acquired signals are stored in a predefined memory space, and when the allocated memory space is full, newly acquired signals are not stored until the microprocessor decides to store another episode of data. Yet another typical mode is the mixed mode, wherein one or more segments of allocated memory space store the acquired signals in queue-loop mode, whereas one or more segments of separately allocated memory space store the data in snapshot mode.

The acquired physiological signals are analyzed by the microprocessor by running programmed algorithms. For example, the microprocessor continuously analyzes the acquired subcutaneous ECG signals to detect the peak of QRS complexes. Such QRS peak detection can be achieved in a variety of different ways. One typical version is to use an Auto-Sensing algorithm that applies a detection hold-off period after each peak detection, and then automatically adjusts the sensing threshold, which is adaptive to the measured peak amplitude of the QRS complex and varies based on predetermined time dependence. An exemplary Auto-Sensing algorithm of this nature is described in U.S. Pat. No. 5,891,048.

The implant device measures the intervals between any two adjacent peaks of the detected QRS complexes, and these intervals are termed RR intervals. These measured RR intervals can be stored in the device memory. Similarly, the microprocessor can also continuously analyze the acquired subcutaneous ECG signals to measure other metrics of the QRS complex, such as the width of the QRS complex, the positive or negative peak amplitude of the QRS complex, the absolute area under the QRS complex, the maximum positive or negative slopes of the QRS complex, the dominant frequency component of the QRS complex, the complexity measures (e.g., sampled entropy) of the QRS complex, and so on. Likewise, the time series of these measured metrics can be stored in the device memory for further analysis.

The implant device also includes a radio frequency (RF) telemetry unit. The RF telemetry unit may be of a type well known in the field for conveying various information from the implant device to the external programmer, and/or for receiving programming parameters from the external programmer and then conveying them to the implant device. In a typical version, the external programmer can interrogate the implant device to get the status of the implant device (e.g., battery status, sensing channel impedance, etc.) and/or the data recorded by the implant device (e.g., peak amplitude of the QRS complexes, statistics of measured RR intervals, etc.). Additionally or alternatively, the external programmer can be used to activate or deactivate selected algorithms or update programmable parameters of the implant device.

In addition, the external portable device can communicate bi-directionally with the implant device through the telemetry unit. Preferably, the data that may be received from or sent to the external portable device is more limited than any data received from or sent to the external programmer.

In a preferred version, the data transmitted from the external portable device to the implant device are simple commands, such as a command to trigger a snapshot of the acquired subcutaneous ECG, to retrieve the most recent diagnostic information from the implanted device, etc. These commands set the implant device into one of a number of modalities wherein each modality is determined and controlled by parameters that are preferably only selectable by a physician operating the external programmer using a secure password or codes.

The data transmitted from the implant device to the external portable device preferably include a simple acknowledgment to confirm receipt of the commands from the external portable device, and signals warning of the detection of abnormal conditions, such as detection of atrial fibrillation (AF), detection of high ventricular rate (HVR), detection of low ventricular rate (LVR), detection of abnormal sensing impedance, detection of abnormal temperature, and so on. Other diagnostic information, such as the AF burden, the frequency of ectopic beats, snapshots of RR intervals or subcutaneous ECG, etc., can also be transmitted to the external portable device. Preferably, a physician operating the external programmer using a secure password or codes can enable or disable communications with the external portable device, as well as controlling the amount of data that can be transmitted from the implant device to the external portable device.

The external portable device has a power source, such as a lithium battery, which provides power to the electrical components of the device. The battery is rechargeable by connecting to an external charger. The external portable device also maintains an internal clock for timing its operations. The overall functioning of the external portable device is controlled by its microprocessor, which reads and performs instructions stored in its associated memory. The instructions stored in memory preferably include instructions defining a communication protocol compatible with the implant device, and instructions defining a communication protocol compatible with the remote service center.

The microprocessor of the external portable device communicates with an I/O control unit to read patient input commands from a keypad, press switches, or other input devices of the control unit. In an exemplary version, one subset of the input commands is designed to configure the external portable device, for example, to turn on or off certain outputs as described hereinafter, or to select specific communication protocols. Another subset of the input commands is designed to establish communication between the external portable device and the remote service center through a remote communication unit. For example, a patient's input can command the external portable device to transmit diagnostic information (retrieved from the implant device) to the remote service center, and wait to receive acknowledgment. A third subset of the commands is designed to establish communication between the external portable device and the implant device through the implant communication unit. For example, an input can command the external portable device to transmit corresponding signals to the implant device to trigger recordation of a snapshot of the subcutaneous ECG, to retrieve diagnostic information from the implant device, etc. The external portable device's implant communication unit may also receive the acknowledgment and related diagnostic information sent from the implant device, and convey these data to the microprocessor for storage in the memory.

In an exemplary version of the invention, upon receiving a predefined warning signal from the implant device (e.g., detection of AF, detection of HVR, detection of LVR, detection of abnormal sensing impedance, detection of abnormal temperature, etc.), the microprocessor of the external portable device communicates with the I/O control unit to generate output perceptible to the patient. Such output can be in the form of a visible message, such as the illumination or blinking of a light emitting diode (LED), or a text message displayed in a liquid crystal display (LCD), or in the form of an audible message such as a beep, ringing tone, or pre-recorded voice messages played by a speaker, or in the form of discernible vibration by a vibrator. According to the patient's preference, one or several types of warning messages can be respectively turned on or off. For example, the visible warning message can be turned on while the audible warning message can be turned off during the night if the patient chooses not to be disturbed during sleep even if the implant device detects AF. Besides generating warning messages, diagnostic information is received from the implant device and stored in memory (e.g., the heart rate), and can also be provided to the patient in the form of visual or audible messages.

The external portable device, via its remote communication unit, can further communicate with the remote service center. Such a remote communication unit can be in the form of a mobile radio network, or a fixed-line telecommunication network, or the internet, as well known in the field of implantable devices. Examples of such long-range communication devices have been described in U.S. Pat. No. 6,470,215, U.S. Pat. No. 6,574,509 and U.S. Pat. No. 6,622,043, incorporated herein by reference.

In one typical version, the external portable device transmits the implant device status information (e.g., battery status, sensing impedance, etc.) as well as relevant diagnostic information (e.g., AF burden, ectopic beat frequency, etc.) to the remote service center according to a predefined transmission frequency and schedule (e.g., every midnight, etc.). In another typical version, the external portable device communicates with the remote service center in a trigger mode, for example, upon receiving a warning signal from the implant device, or upon a patient activated trigger. In such cases, the external portable device transmits critical diagnostic information stored in the device memory (e.g., AF burden, mean heart rate, the subcutaneous ECG snapshot, etc.) to the remote service center.

The remote service center receives the information via compatible communication protocols, and then sends an acknowledgment back to the external portable device, which may generate visible or audible output indicating receipt of the acknowledgment. The data received by the remote service center is stored in a central database, and is promptly presented to the patient's physician or responsible expert through proper means, such as fax, email, and text message (as known in the field). By reviewing the received diagnostic information, the physician can evaluate the patient's condition and provide expert advice to the patient, who will likely wish to contact the physician before taking any action in response to the warning signals generated by the external portable device.

The method and device for noise detection from subcutaneous electrocardiogram recordings is further described below. It should be understood that the principles of the invention are also applicable to noise detection from electrocardiograms (ECG) in general, and in particular from intracardiac electrograms recorded by implantable pacemakers or defibrillators, and/or from surface electrocardiograms recorded using conventional ECG machines, bedside ECG monitors, Holter ECG devices, automatic external defibrillators, etc.

In the invention, the noise condition of a physiological signal is continuously evaluated on a sample-by-sample basis. FIGS. 2 to 8 illustrate a first version featuring only one upper noise threshold NZTHRESH and one lower noise threshold –NZTHRESH for a signal amplitude. FIGS. 9 to 14 illustrate a second version featuring two upper noise thresholds HITHRESH and LOTHRESH, and two lower noise thresholds –HITHRESH and –LOTHRESH, for a signal amplitude. Additional thresholds are possible by extending the principles described below.

Figure 2:
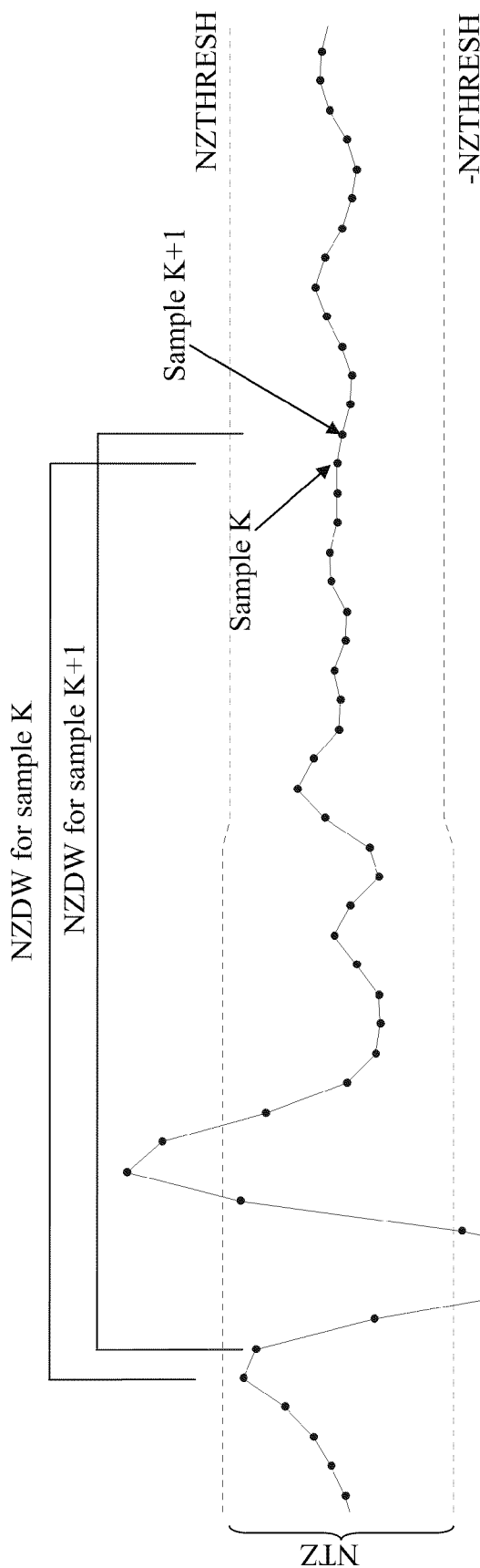
FIG. 2 illustrates the concept of a sample-by-sample noise detection window NZDW. The noise threshold NZTHRESH and a noise tolerance zone NTZ are also illustrated.
Figure 9:
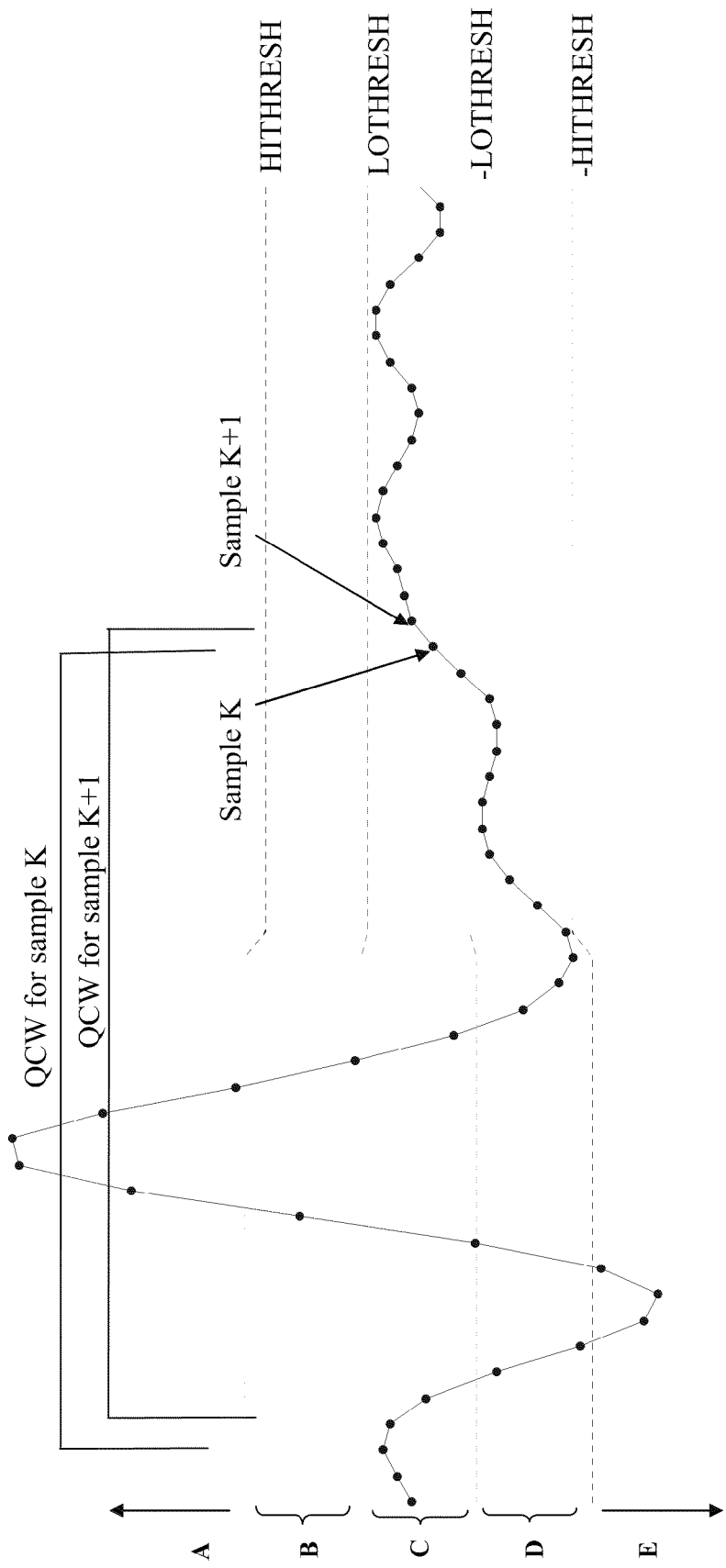
FIG. 9 illustrates the concept of the sample-by-sample quality check window QCW (also referred to above as a noise detection window NZDW) and the space segmentation by high noise threshold HITHRESH and low noise threshold LOTHRESH vectors.

As illustrated in FIGS. 2 and 9, each sample is preceded by a noise detection window (quality check window), denoted NZDW in FIG. 2 and denoted QCW in FIG. 9, that has a user-programmable window length. In a typical version, the noise detection window NZDW is 125 ms, which corresponds to 32 samples at 256 Hz. In an alternative version, the noise detection window NZDW is 250 ms, which corresponds to 64 samples at 256 Hz. The noise detection window (NZDW) serves as a quality check window (QCW), and these terms can be used interchangeably, with this document generally using NZDW (or QCW) to indicate the duration (in time and/or number of samples) of the window.

Figure 3:
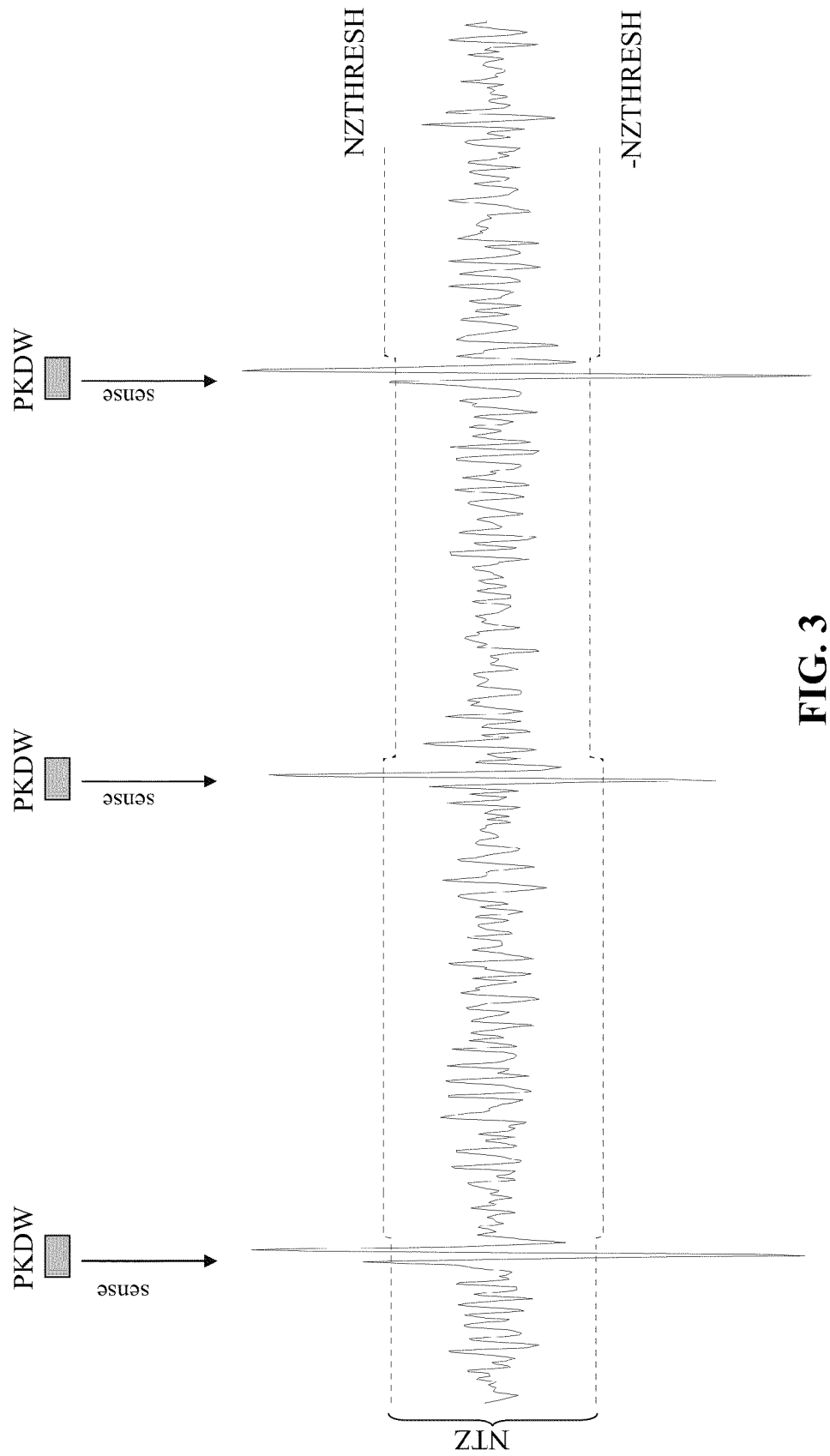
FIG. 3 illustrates the peak detection window PKDW around each beat detection, the adaptive noise threshold NZTHRESH, and the associated noise tolerance zone NTZ.
Figure 10:
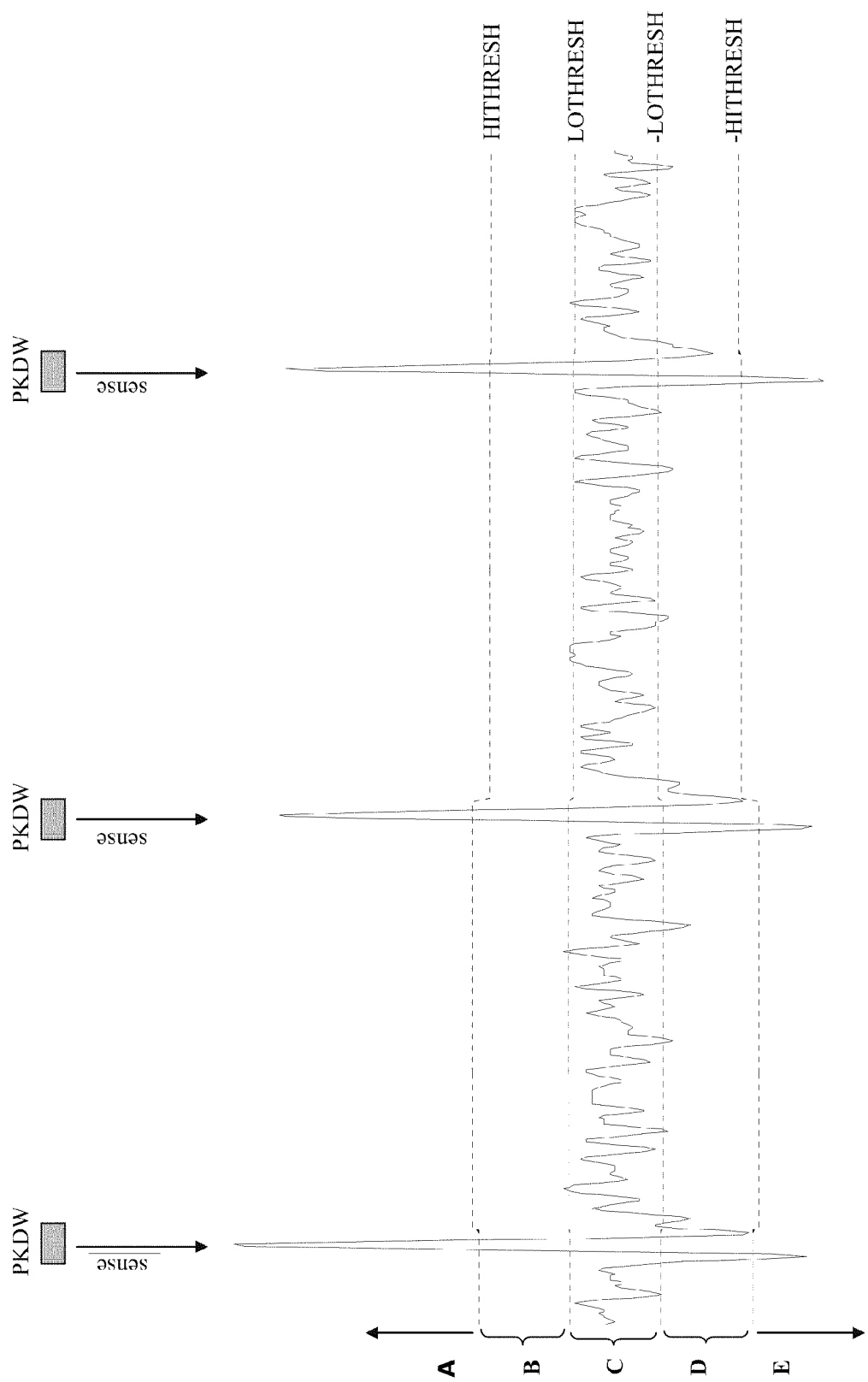
FIG. 10 illustrates the peak detection window PKDW around each beat detection, the adaptive HITHRESH and LOTHRESH vectors, and the associated subspaces.

For a recorded subcutaneous ECG signal, the device independently performs beat detection and generates sense markers. As illustrated in FIGS. 3 and 10, the device starts a peak detection window PKDW after each beat detection, triggered by the amplitude of a sample crossing a beat detection threshold, to search for the absolute peak amplitude PEAK of the signal. The peak detection window PKDW spans from T1 before the sense marker to T2 after the sense marker, with both T1 and T2 being user-programmable parameters. In a typical version, T1 is 40 ms and T2 is 60 ms. In another typical version, T1 is 0 ms and T2 is 200 ms. Typically, the found absolute peak signal amplitude value PEAK is the largest absolute signal amplitude of the QRS complex. Even if the peak detection window PKDW does not cover the whole QRS complex, the found absolute peak amplitude value PEAK still represents the signal amplitude around the sense marker.

In the version of FIG. 2, the device maintains a (single) upper threshold referred to as the noise threshold NZTHRESH, with a value that adapts to the signal amplitude. The device further maintains a (single) lower threshold having the same magnitude as the noise threshold NZTHRESH but having the opposite sign, and thus is called −NZTHRESH with it here being assumed that the ECG signal has zero baseline after applying the front-end high-pass filter). The positive noise threshold NZTHRESH and the negative noise threshold −NZTHRESH form a noise tolerance zone NTZ, and define three amplitude ranges, namely a high amplitude range for amplitudes above NZTHRESH, a medium amplitude range corresponding to the noise tolerance zone NTZ, and a low amplitude range for amplitudes below −NZTHRESH. During device initialization, the noise threshold NZTHRESH is set to MIN_NZTHRESH, which is a user-programmable minimum noise threshold. For example, the minimum noise threshold MIN_NZTHRESH can be selected from a list of predefined voltage values such as 0.025 mV, 0.05 mV, 0.075 mV, 0.1 mV, etc. Then after detection of each beat, the noise threshold NZTHRESH is automatically adapted with respect to the detected absolute peak signal amplitude value PEAK as described below.

In the version of FIG. 9, the device maintains at least two positive noise thresholds or noise threshold vectors, a high noise threshold HITHRESH and a low noise threshold LOTHRESH, both of which adapt to changing signal amplitudes. Two negative thresholds −HITHRESH and −LOTHRESH are also provided, with the negative thresholds in this example having the same magnitudes as the positive thresholds (but opposite signs). Typically, the magnitude of HITHRESH is larger than LOTHRESH. During device initialization, the high noise threshold HITHRESH is set to a minimum value MIN_HITHRESH, and the low noise threshold LOTHRESH is set to a minimum value MIN_LOTHRESH. Both MIN_HITHRESH and MIN_LOTHRESH are user-programmable, and they respectively represent the minimum thresholds that are allowed for HITHRESH and LOTHRESH. For example, the MIN_HITHRESH can be selected from a list of predefined voltage values such as 0.025 mV, 0.05 mV, 0.075 mV, 0.1 mV, etc, and the MIN_LOTHRESH can be defined as a fraction (e.g. 50%) of the MIN_HITHRESH.

In the following discussions, it is assumed that the ECG signal has zero baseline after applying the front-end high-pass filter, thus the noise thresholds HITHRESH and −HITHRESH are symmetric around the baseline, and the noise thresholds LOTHRESH and −LOTHRESH are also symmetric around the baseline. As depicted in FIG. 9, the noise thresholds HITHRESH and LOTHRESH divide the signal space into five non-overlapping amplitude ranges, which will also be referred to as subspaces: A is the subspace (amplitude range) above HITHRESH, B is the subspace (amplitude range) between LOTHRESH and HITHRESH, C is the subspace (amplitude range) between −LOTHRESH and LOTHRESH, D is the subspace (amplitude range) between −LOTHRESH and −HITHRESH, and E is the subspace (amplitude range) below −HITHRESH. If the baseline of the ECG signal is not zero, the threshold vectors can be defined in an asymmetric manner, preferably such that subspace C encompasses the baseline.

After each beat detection, the noise threshold(s) NZTHRESH or both HITHRESH and LOTHRESH are automatically adapted to the newly-found absolute peak signal amplitude value PEAK as described below.

First looking to the version of the invention of FIGS. 2 to 8, as illustrated in FIG. 3, after detection of each beat, the noise threshold NZTHRESH remains unchanged during the peak detection window PKDW. Immediately after the peak detection window PKDW, the noise threshold NZTHRESH is recalculated based on the previous NZTHRESH value, the current absolute peak amplitude value PEAK (denoted as NEW_PEAK), and the smoothed PEAK amplitudes of the past beats (denoted as OLD_PEAK). In a preferred approach, the noise threshold NZTHRESH is calculated in 3 steps:

$$\text{NEW\_PEAK}=\min(\text{NEW\_PEAK}, p*\text{OLD\_PEAK}); \quad (1.1)$$

$$\text{OLD\_PEAK}=\text{OLD\_PEAK}*c1+\text{NEW\_PEAK}*c2; \quad (1.2)$$

$$\text{NZTHRESH}=\max(\text{MIN\_NZTHRESH}, \text{OLD\_PEAK}*f); \quad (1.3)$$

Similarly, in the version of the invention of FIGS. 9 to 14, FIG. 10 shows that after each beat detection, the noise thresholds HITHRESH and LOTHRESH remain unchanged during the peak detection window PKDW. Immediately after the peak detection window PKDW, the noise threshold HITHRESH is recalculated based on the previous HITHRESH value, the present absolute peak amplitude PEAK (denoted as NEW_PEAK), and the smoothed PEAK amplitudes of the past beats (denoted as OLD_PEAK). Similarly, the noise threshold LOTHRESH is recalculated based on the previous LOTHRESH value, the present absolute peak amplitude PEAK (denoted as NEW_PEAK), and the smoothed PEAK amplitudes of the past beats (denoted as OLD_PEAK). Preferably, the noise thresholds HITHRESH and LOTHRESH are calculated in following steps:

$$\text{NEW\_PEAK}=\min(\text{NEW\_PEAK}, p*\text{OLD\_PEAK}); \quad (2.1)$$

$$\text{OLD\_PEAK}=\text{OLD\_PEAK}*c1+\text{NEW\_PEAK}*c2; \quad (2.2)$$

$$\text{HITHRESH}=\max(\text{MIN\_HITHRESH}, \text{OLD\_PEAK}*fh); \quad (2.3)$$

$$\text{LOTHRESH}=\max(\text{MIN\_LOTHRESH}, \text{OLD\_PEAK}*fl); \quad (2.4)$$

In Equations (1.1) and (2.1), p is a user-programmable parameter that is greater than 1.0. Preferably, p is set to 1.25 or 1.5. Therefore, the new absolute peak amplitude NEW_PEAK is limited to the minimum of PEAK amplitude measured for the current beat and the OLD_PEAK amplitude scaled by the coefficient p. This prevents the abrupt increase of HITHRESH or LOTHRESH due to the detection of a very large PEAK amplitude (e.g., due to impulse noise).

In Equations (1.2) and (2.2), c1 and c2 are also user-programmable weighting coefficients that are between 0 and 1, wherein $c1+c2=1.0$. In a preferred version, $c1=0.5$ and $c2=0.5$. Alternative settings can also be used, for example, $c1=0.75$ and $c2=0.25$, or $c1=0.25$ and $c2=0.75$, etc. This equation calculates the weighted average of the OLD_PEAK and the NEW_PEAK, and the result is assigned to OLD_PEAK. Therefore, OLD_PEAK represents the smoothed PEAK amplitudes of the past beats. The updated OLD_PEAK is then maintained until the next beat detection.

In Equations (1.3), (2.3) and (2.4), f, fh, and fl are also user-programmable parameters that are less than 1.0. In a preferred version, f or fh is set to 0.375 for calculating HITRRESH, and fl is set to 0.125 for calculating LOTHRESH. Other exemplary settings can also be used, for example fh=0.5, fl=0.25, etc. Therefore, equation (1.3) or (2.3) sets NZTHRESH or HITHRESH, respectively, to a predefined percentage of the updated OLD_PEAK with the lower limit of the predefined MIN_NZTHRESH or MIN_HITHRESH, respectively, while equation (2.4) sets LOTHRESH to another predefined percentage of the updated OLD_PEAK with the lower limit of the predefined MIN_LOTHRESH.

Because the OLD_PEAK represents the weighted average of the signal peak amplitude, the calculated noise threshold NZTHRESH represents a tolerance level for noise. In other words, for a relatively clean ECG signal with high SNR, most samples between adjacent QRS complexes are expected to be bounded by ±NZTHRESH and thus fall into the medium amplitude range as used in the version of FIG. 2. On the other hand, for a relatively noisy ECG signal with low SNR, many samples between adjacent QRS complexes are expected to fall outside the noise tolerance zone NTZ, that is, outside the medium amplitude range.

Similarly, because OLD_PEAK represents the weighted average of the signal peak amplitude, the calculated noise thresholds HITHRESH and LOTHRESH represent two different tolerance levels for noise. In other words, for a relatively clean ECG signal with high SNR, most samples between adjacent QRS complexes are expected to fall in the subspace C, that is, the medium amplitude range according to FIG. 9. On the other hand, when noise is present and SNR is low, many samples between adjacent QRS complexes are expected to fall in the subspaces B and D, and even in the subspaces A and E.

Figure 4:
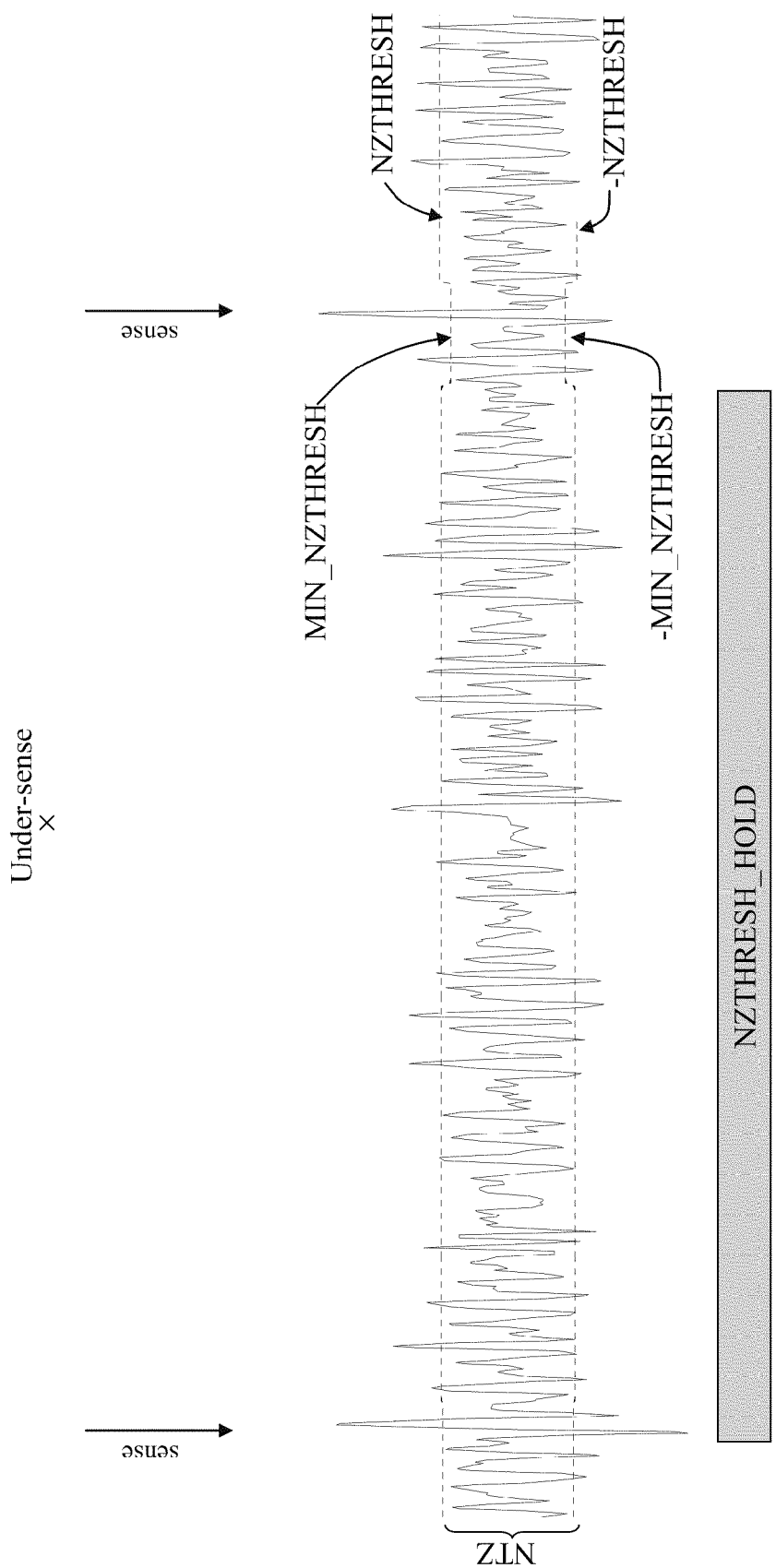
FIG. 4 illustrates a situation wherein the NZTHRESH is changed to MIN_NZTHRESH when no beat is detected after the duration of NZTHRESH_HOLD.

In the version of FIGS. 3-4, either the noise threshold NZTHRESH is kept constant until the next beat detection when it is again updated based on equations (1)-(3), or NZTHRESH is lowered to MIN_NZTHRESH when no beat is detected after a user-programmable reset period (NZTHRESH_HOLD). In a preferred version, the reset period NZTHRESH_HOLD is set to 2 seconds. Alternative settings can also be used, for example, the reset period NZTHRESH_HOLD can be set to 1 second, 2.5 seconds, etc. As illustrated in FIG. 4, the device sometimes may under-sense the QRS complex (marked by the vertical dashed line and a cross). In such cases, the noise threshold NZTHRESH may not be properly adapted to the signal amplitude, and thus may be too high to detect noise. Therefore, by lowering the NZTHRESH to MIN_NZTHRESH after the reset period NZTHRESH_HOLD, the device can become more alert to noise conditions.

Figure 11:
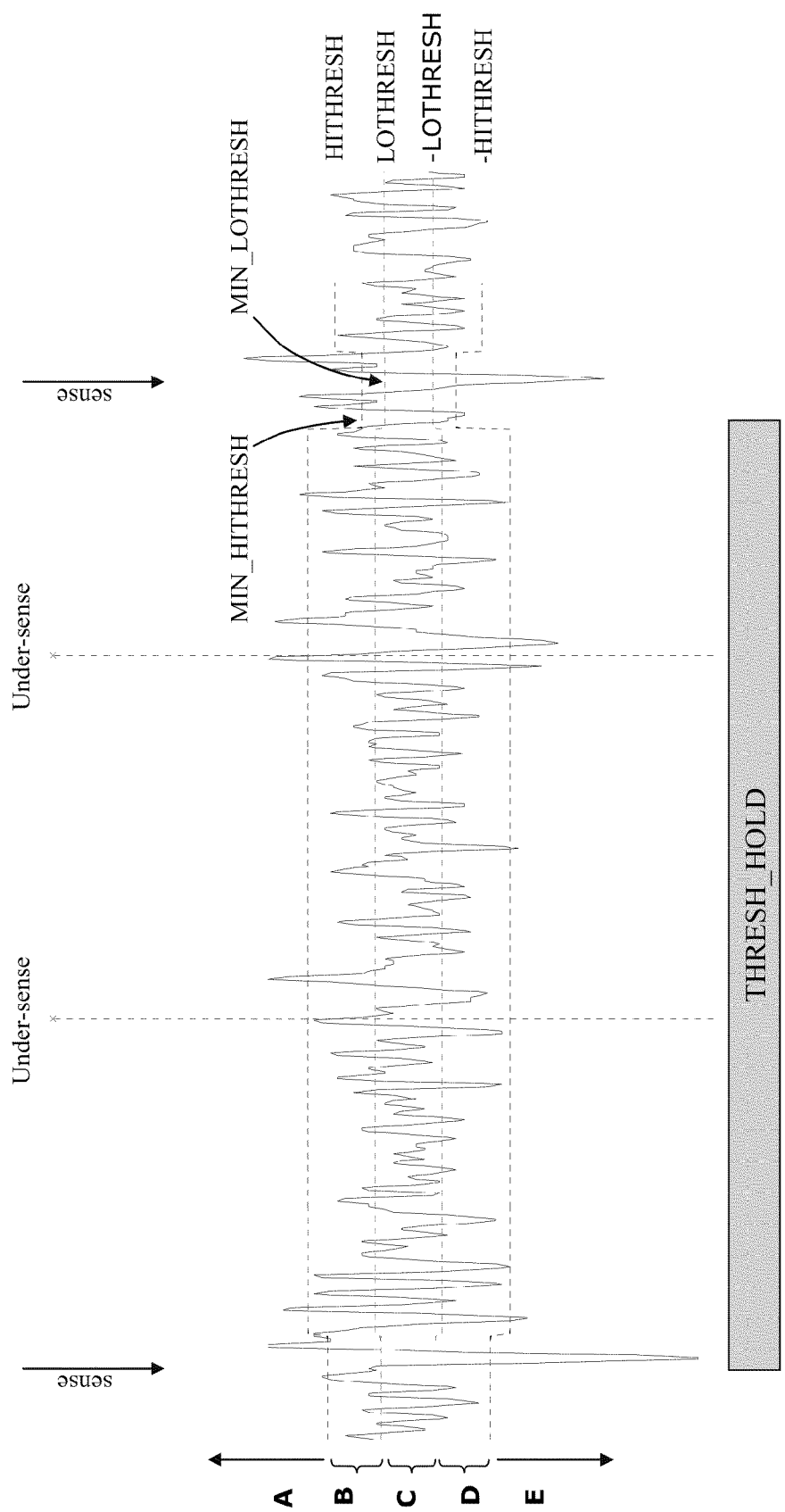
FIG. 11 illustrates the case that the HITHRESH and LOTHRESH are changed to their respective minimum values when no beat is detected after the duration of THRESH_HOLD.

Similarly, in the version of FIGS. 9-10, either the noise thresholds HITHRESH and LOTHRESH are kept constant until the next beat detection when they are again updated based on equations (2.1) to (2.4), or they are reset to their respective minimum threshold values when no beat is detected after a user-programmable reset period (THRESH_HOLD). In a preferred version, the reset period THRESH_HOLD is set to 2 seconds. Alternative settings can also be used, for example, the reset duration THRESH_HOLD can be set to 1 second, 2.5 seconds, etc. As illustrated in FIG. 11, the device sometimes may under-sense the QRS complexes (marked by the vertical dashed lines). In such cases, the noise thresholds HITHRESH and LOTHRESH may not be properly adapted to the signal amplitude. Therefore, by lowering HITHRESH to MIN_HITHRESH and LOTHRESH to MIN_LOTHRESH after the reset period THRESH_HOLD, the device can become more alert to noise conditions.

Noise condition evaluation (signal quality evaluation) will now be described, starting with a discussion of noise condition evaluation for the version of FIGS. 2-8.

Figure 5A:
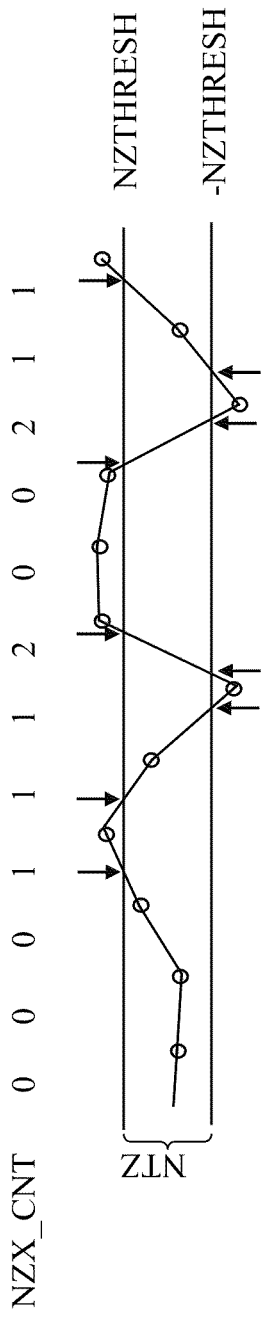
FIG. 5A illustrates the method of counting noise threshold crossings.
Figure 5B:
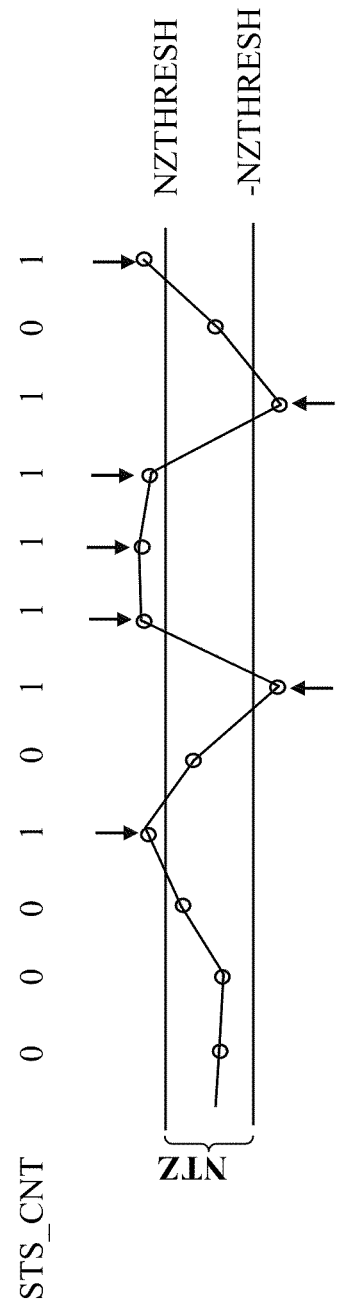
FIG. 5B illustrates the method of counting supra-threshold samples.

For each noise detection window NZDW, the noise condition is evaluated by two metrics: the noise threshold crossing count (NZX_CNT), and the supra-threshold sample count (STS_CNT). FIG. 5A schematically illustrates a method of counting noise threshold crossings, wherein each arrow points to a noise threshold crossing. FIG. 5B illustrates a method of counting supra-threshold samples, wherein each arrow points to a supra-threshold sample.

Assume the current sample amplitude is X(k), and the previous sample amplitude is X(k−1). The corresponding noise thresholds for the two samples are NZTHRESH(k) and NZTHRESH(k−1), respectively. The supra-threshold sample count STS_CNT for the k-th sample is set to 1 if $X(k) \geq \text{NZTHRESH}(k)$ OR $X(k) \leq -\text{NZTHRESH}(k)$ Otherwise, if $-\text{NZTHRESH}(k-1) < X(k) < \text{NZTHRESH}(k-1)$, the supra-threshold sample count STS_CNT for the k-th sample is set to 0.

The noise threshold crossing count NZX_CNT for the k-th sample is set to 1 if $X(k) \geq \text{NZTHRESH}(k)$ OR $X(k) \leq -\text{NZTHRESH}(k)$

AND $-\text{NZTHRESH}(k-1) < X(k-1) < \text{NZTHRESH}(k-1)$

On the other hand, the noise threshold crossing count NZX_CNT for the k-th sample is set to 2 if $X(k) \geq \text{NZTHRESH}(k)$ AND $X(k-1) \leq -\text{NZTHRESH}(k-1)$

OR $X(k) \leq -\text{NZTHRESH}(k)$ AND $X(k-1) \geq \text{NZTHRESH}(k-1)$

Otherwise, if both X(k) and X(k−1) are within the NTZ, or both are ≥NZTHRESH or both are ≤−NZTHRESH, the noise threshold crossing count NZX_CNT for the k-th sample is set to 0.

For the version of FIGS. 2-8, both the noise threshold crossing count NZX_CNT and the supra-threshold sample count STS_CNT are continuously assessed for each sample. Specifically, the device maintains two first-in-first-out (FIFO) buffers that respectively store the noise threshold crossing count NZX_CNT and the supra-threshold sample count STS_CNT for all samples within the noise detection window NZDW. The sum of the noise threshold crossing count NZX_CNT (denoted as NZX_SUM, the noise threshold crossing sum) and the sum of the supra-threshold sample count STS_CNT (denoted as STS_SUM, the supra-threshold sample sum) for all samples within the noise detection window NZDW are calculated. The noise condition for the specific noise detection window NZDW is indicated when any one of the following three conditions is met:

(1) the noise threshold crossing sum NZX_SUM exceeds a first user-programmed threshold (TX1); OR (2) the supra-threshold sample sum STS_SUM exceeds a second user-programmed threshold (ST1); OR (3) the noise threshold crossing sum NZX_SUM exceeds a third user-programmed threshold (TX2) AND the supra-threshold sample sum STS_SUM exceeds a fourth user-programmed threshold (ST2).

Preferably, the thresholds are set so that TX2≤TX1 and ST2≤ST1. For a noise detection window NZDW having 32 samples with sampling frequency 256 Hz (i.e., the noise detection window NZDW has a duration of 125 ms), a typical set of thresholds is TX1=10, TX2=25, TX3=8, and TX4=8. Conditions (1) and (3) are mainly useful to detect high frequency noise, whereas the condition (2) is mainly useful to detect saturation noise.

Figure 6:
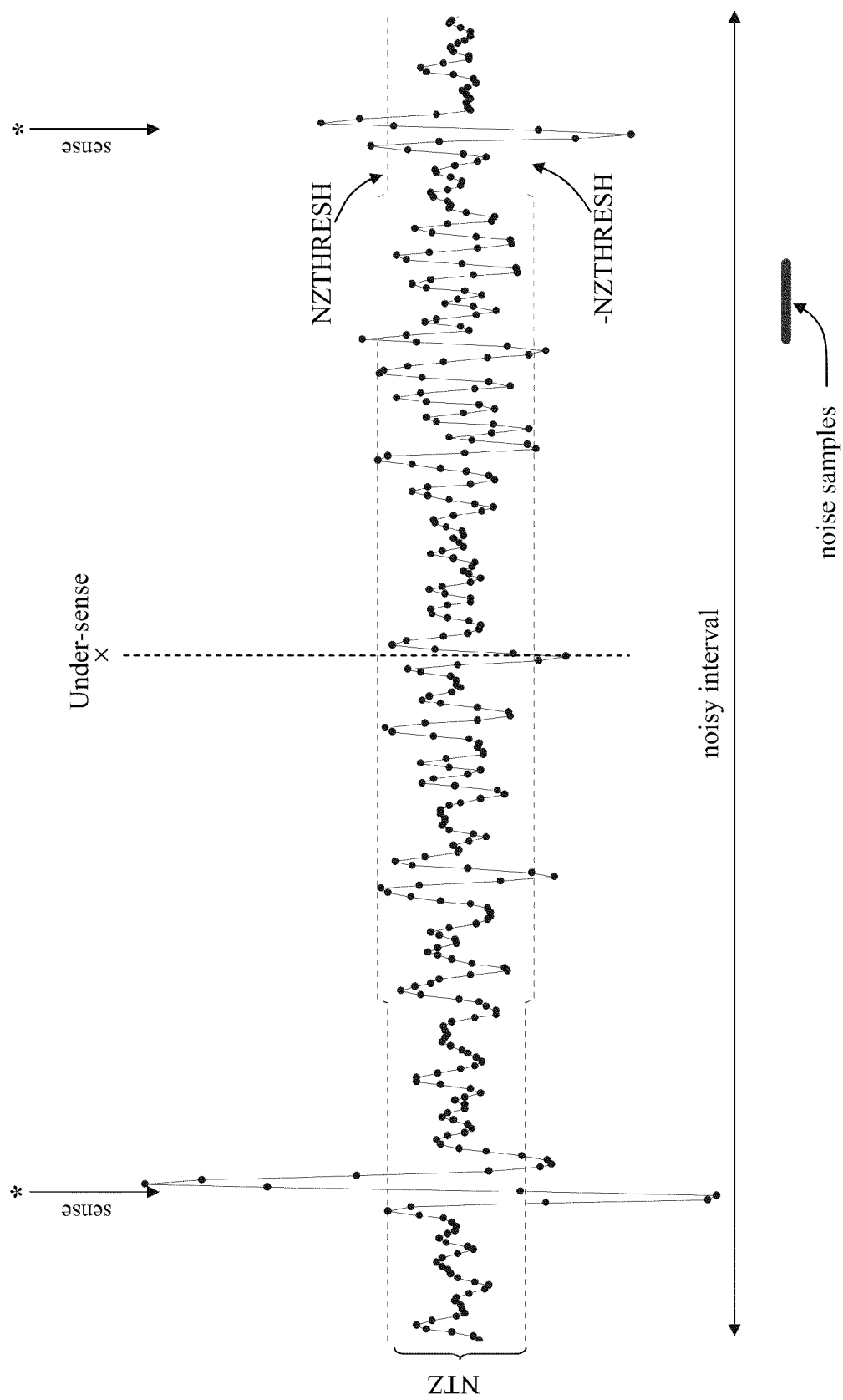
FIG. 6 shows an example of the flagging of noise samples, unreliable detections, and the noisy interval.

Referring to FIG. 6, in a preferred version, when a noise condition is indicated for any noise detection window NZDW associated with a specific sample, this sample is considered to be noise sample. Then the detected beats immediately before and immediately after this noise sample are labeled as unreliable detections (marked by * in FIG. 6), and the interval between this pair of unreliable detections is classified as a noisy interval. In addition, one or more intervals before the first unreliable detection, and/or one or more intervals after the second unreliable detection, can also be classified as noisy intervals.

Figure 7:
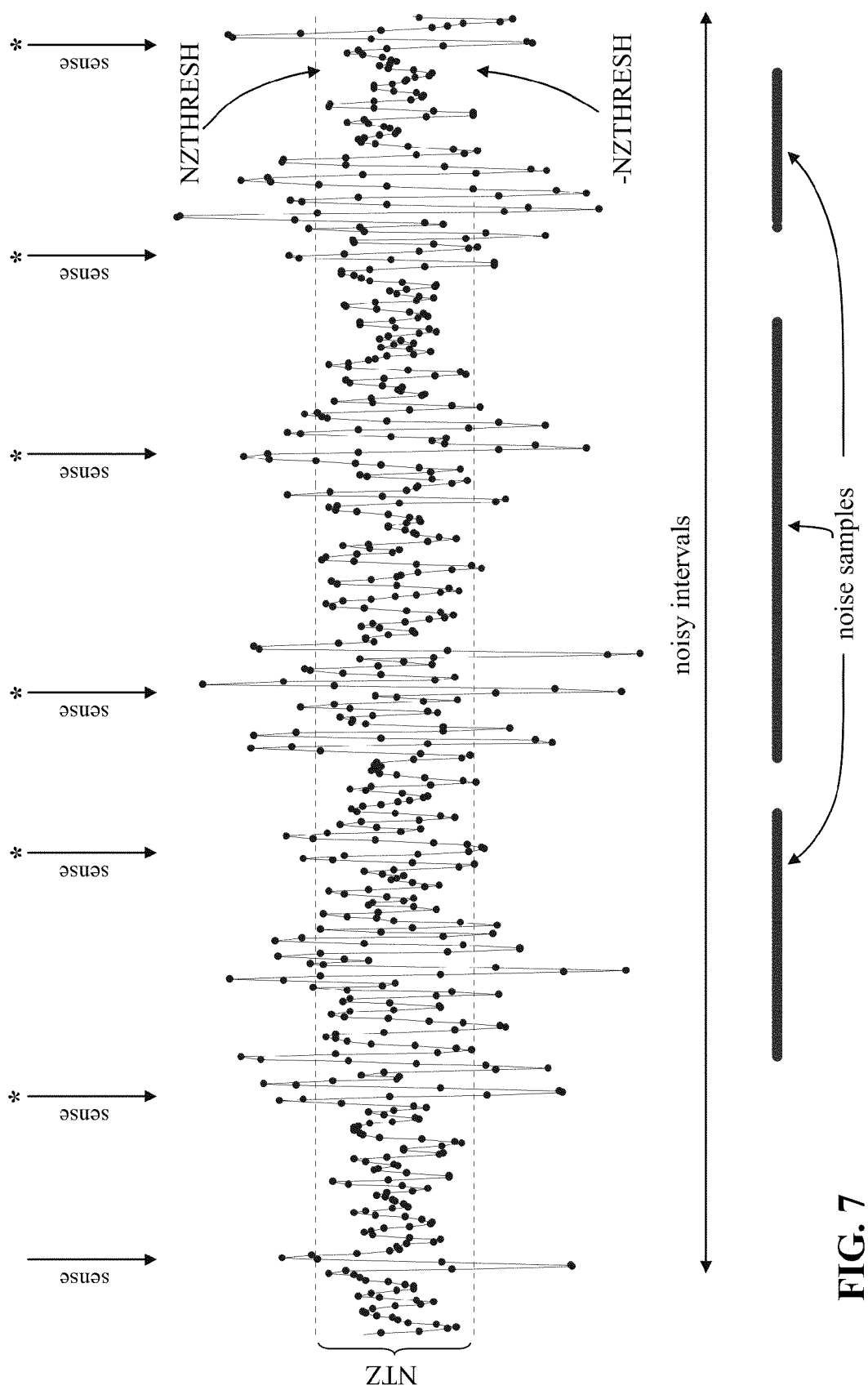
FIG. 7 shows another example of the flagging of noise samples, unreliable detections, and noisy intervals.

Referring to FIG. 7, in another preferred version, noise detection is evaluated on a moving window basis. The moving window consists of Y samples. When X out of Y samples are determined as noise samples, the noise condition is confirmed. For example, if Y=64 and X=32, the noise condition is indicated when more than half of the samples in the moving window are noisy samples. The detected beats immediately before and immediately after this window can then be classified as unreliable detections (marked by * in FIG. 7), and the intervals associated with any pair of unreliable detections can be classified as noisy intervals.

Figure 8:
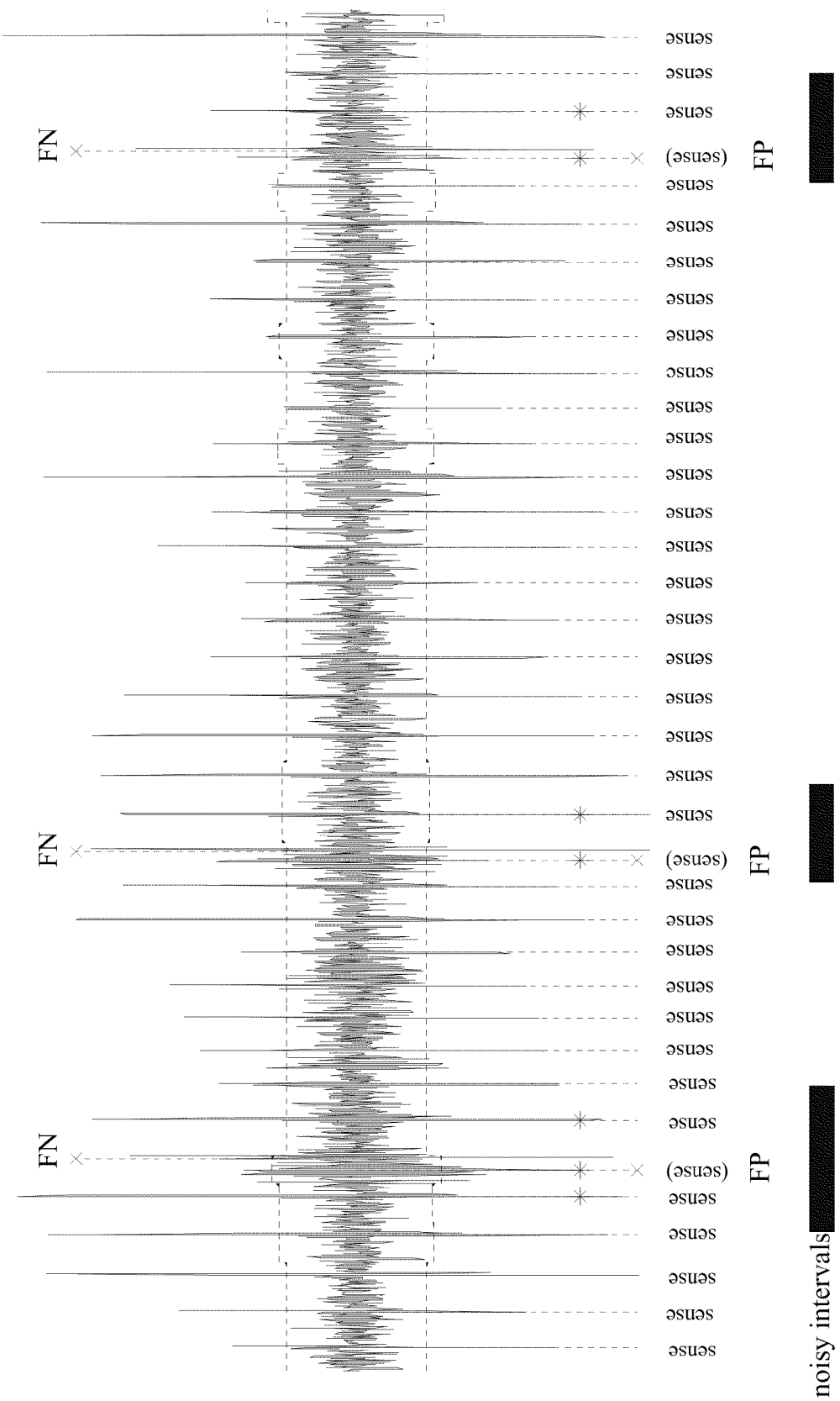
FIG. 8 shows a typical example of an ECG noise detection result.

FIG. 8 shows an example of an ECG noise detection result. In this example, beat detections are labeled by sense markers, marked by downward dashed lines. False positive (FP) detections occur 3 times, indicated by "sense" in parenthesis and an "X" marker at the end of the downward dashed line. False negatives (FN, or under-sensing) occur in 3 beats marked by upward dashed lines ending with the "X" marker. According to the noise detection algorithm described above, 7 senses are determined as unreliable detections (marked by * on the downward dashed lines), and the intervals associated with these unreliable detections are classified as noisy intervals. These unreliable senses and the associated noisy intervals are preferably excluded from rate and rhythm analysis, or are otherwise at least treated with less confidence, therefore improving the diagnostic accuracy of the device.

Figure 12:
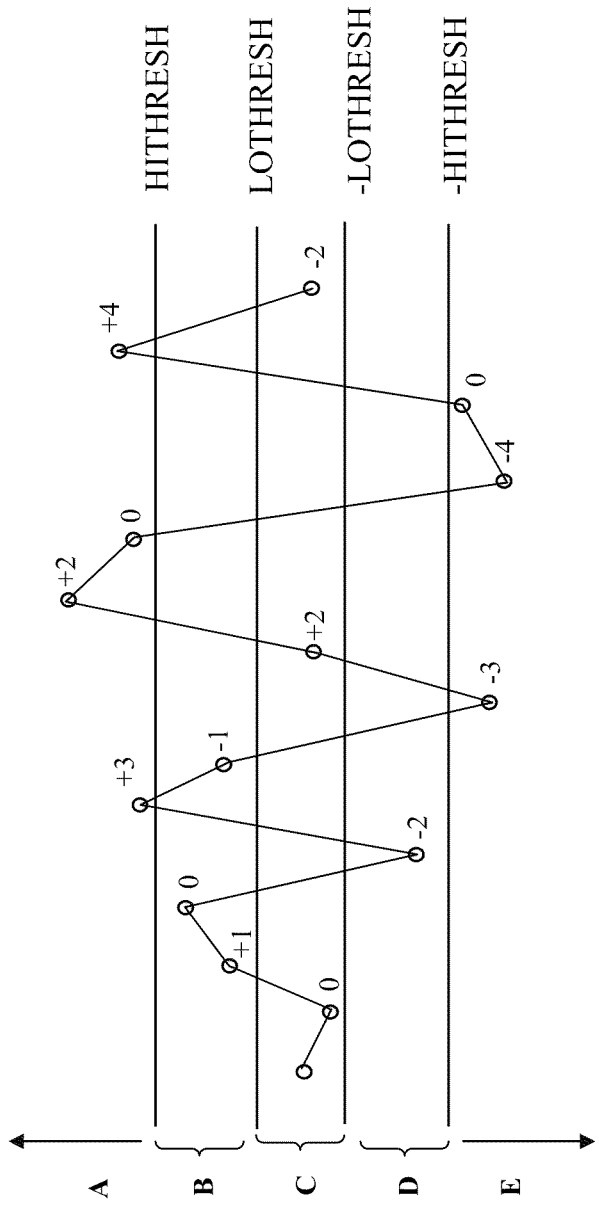
FIG. 12 illustrates a method of converting signal samples to symbols, and translating the signal dynamics to symbol change steps.

Signal quality evaluation according to the version of FIGS. 9-14 will now be reviewed. For each quality control window QCW (which, as previously noted, can also be referred to as a noise detection window NZDW), signal quality can be evaluated by means of a symbolic dynamics approach. FIG. 12 illustrates the basic concept of converting the signal samples to symbols, and then extracting the symbolic dynamics.

First, each signal sample is converted to one of five symbols according to which subspace (amplitude range) it belongs to. In other words, a sample is assigned a symbol 'a' if it falls in subspace A, or 'b' if it falls in subspace B, or 'c' if it falls in subspace C, or 'd' if it falls in subspace D, or 'e' if it falls in subspace E. Therefore, in FIG. 12, the 15 signal samples are converted to a string of 15 symbols: c-c-b-b-d-a-b-e-c-a-a-e-e-a-c.

Then for any two adjacent sample pairs, their difference is coded based on the symbol change step (SCS). The symbol change step SCS is a threshold crossing count (NZX_CNT) reflecting the number of thresholds between each two adjacent signal samples of each sample pair. If two adjacent signal samples forming a sample pair fall into the same amplitude range, there is no threshold between these samples and thus no symbol change (e.g. 'a-a'), and thus the threshold crossing count SCS is set to 0. If the symbol change is one step (e.g., 'a-b'), that is, if there is one threshold between the adjacent signal samples of a sample pair, then the threshold crossing count SCS is set to 1. If the symbol change is two steps (e.g., 'a-c'), that is, if there are two thresholds between the adjacent signal samples of a sample pair, then the threshold crossing count SCS is set to 2. If the symbol change is three steps (e.g. 'a-d'), that is, if there are three thresholds between the adjacent signal samples of a sample pair, then the threshold crossing count SCS is set to 3. If the symbol change is four steps (e.g., 'a-e'), that is, if there are four thresholds between the adjacent signal samples of a sample pair, then the threshold crossing count SCS is set to 4. Table 1 below lists all possible symbol pairs and their respective SCS codes. The SCS sign indicates the direction of amplitude change, thus a positive SCS indicates amplitude increase across at least one threshold between the sample pair, and negative SCS indicates amplitude decrease across at least one threshold between the sample pair. Therefore, in FIG. 12, the 14 sample pairs (excluding the first sample) can be translated to a set of SCS codes: {0, +1, 0, −2, +3, −1, −3, +2, +2, 0, −4, 0, +4, −2}, each SCS code reflecting a threshold crossing count. The sequence of SCS codes (threshold crossing counts NZX_CNT) eliminate the detailed signal amplitude information, but keep the robust properties of the signal dynamics by a coarse-graining of the measurements.

TABLE 1

Symbol pairs and the corresponding SCS codes

| SCS | 0 | +1 | +2 | +3 | +4 | −1 | −2 | −3 | −4 |
|---|---|---|---|---|---|---|---|---|---|
| Symbol pairs | a-a | b-a | c-a | d-a | e-a | a-b | a-c | a-d | a-e |
| | b-b | c-b | d-b | e-b | | b-c | b-d | b-e | |
| | c-c | d-c | e-c | | | c-d | c-e | | |
| | d-d | e-d | | | | d-e | | | |
| | e-e | | | | | | | | |

Figure 13:
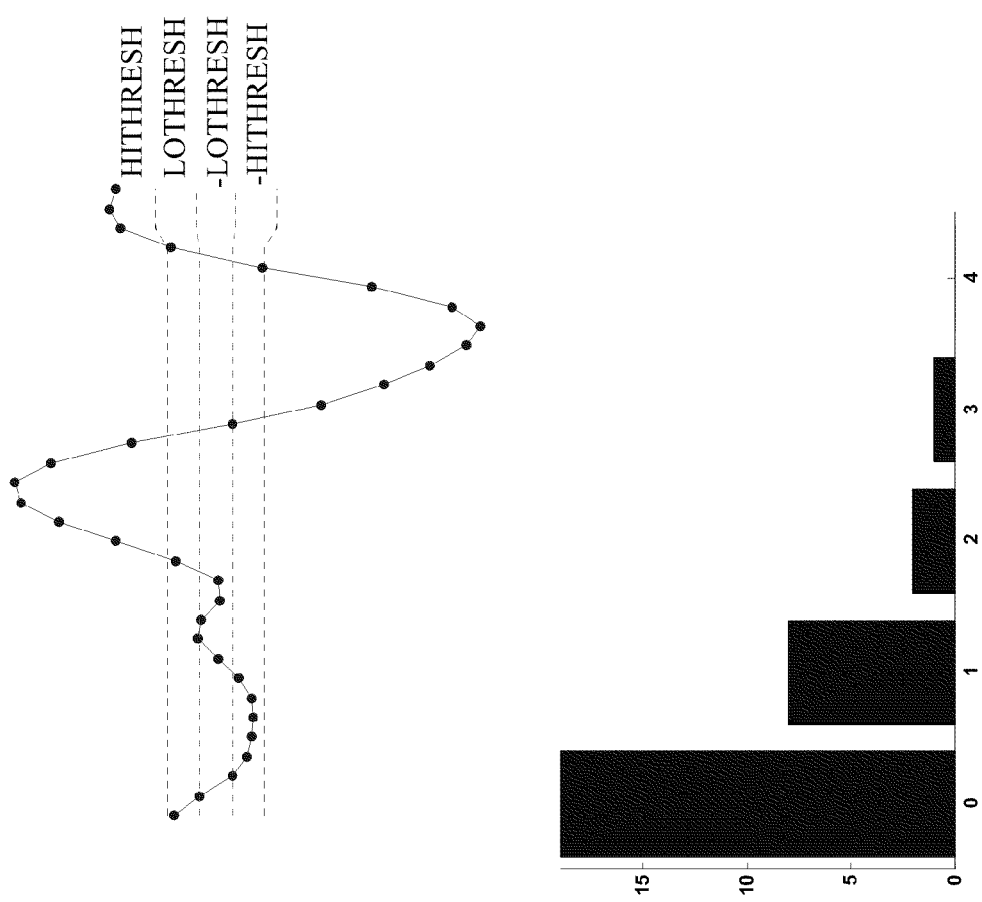
FIG. 13 illustrates a method of constructing a histogram of symbol change step for a given QCW.

For each quality control window QCW, the corresponding sequence of SCS codes (threshold crossing counts NZX_CNT) is then analyzed. In an exemplary approach, a histogram of absolute SCS codes is generated. FIG. 13 illustrates one example in which 32 sample pairs result in a distribution of absolute SCS. In this example, 21 sample pairs have no symbol change (SCS=0), 8 sample pairs have one-step symbol change (SCS=+1 or −1), 2 sample pairs have two-step symbol change (SCS=+2 or −2), and 1 sample pair has three-step symbol change (SCS=+3 or −3). No sample pair has four-step symbol change (SCS=+4 or −4).

Next, a complexity index (CI) (or weighted noise threshold crossing sum NZX_SUM) is calculated to quantify the signal quality for the quality control window QCW. Higher complexity index CI indicates lower signal quality, whereas lower complexity index CI indicates higher signal quality. According to a typical version of the present invention, the complexity index CI is calculated as the weighted sum of the absolute SCS counts:

$$CI = w1*SCS1 + w2*SCS2 + w3*SCS3 + w4*SCS4 \qquad (5)$$

Here SCS1 is the total count of SCS=1 and SCS=−1, SCS2 is the total count of SCS=+2 and SCS=−2, SCS3 is the total count of SCS=+3 and SCS=−3, and SCS4 is the total count of SCS=+4 and SCS=−4. Coefficients w1, w2, w3, and w4 are predefined values that assign desired weights to different symbol change steps. In a typical example, w1=1, w2=4, w3=8, and w4=16.

The complexity index CI is continuously evaluated to monitor the signal quality. Specifically, after receiving each signal sample, the device examines the past samples in the associated quality control window QCW. All samples in the quality control window QCW are converted to symbols and the symbolic dynamics are represented by a sequence of SCS codes. Then the histogram of absolute SCS is constructed and the corresponding complexity index CI is calculated. Higher CI indicates lower signal quality, whereas lower CI indicates higher signal quality. The sample-by-sample complexity index CI can then be compared to a predefined CI threshold to determine whether the ECG signal has sufficient quality for reliable cardiac beat detection.

Figure 14:
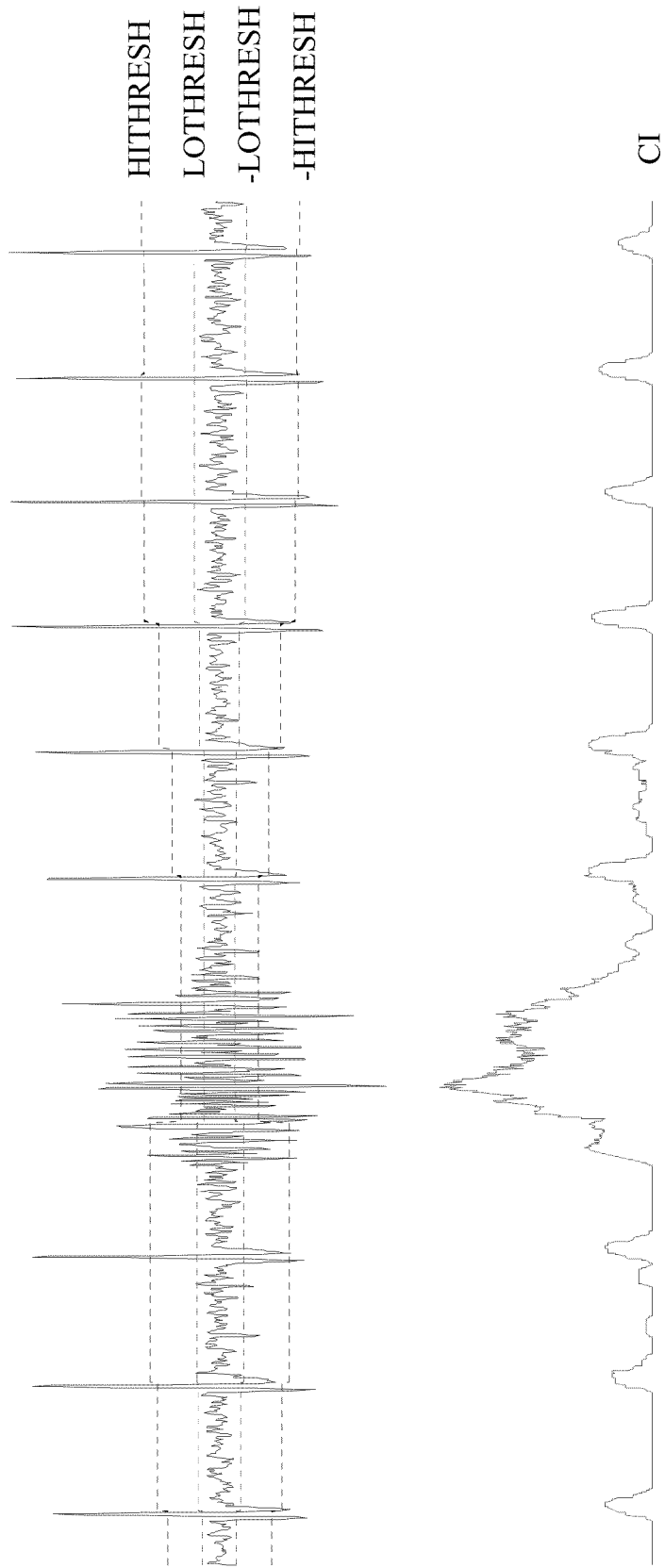
FIG. 14 shows an example of an ECG recording with a burst of noise, and the calculated complexity index which can be used to quantify the signal quality.

FIG. 14 shows an example where a segment of a subcutaneous ECG is shown in the top trace (together with the adaptive noise thresholds), and the calculated complexity index CI is plotted in the bottom trace. Clearly, the complexity index CI remains small for most cardiac cycles, with only slight increase during the QRS complexes. In contrast, the burst of noise (after the third QRS complex) is associated with a sharp increase of the complexity index CI.

It should be understood that the foregoing description merely presents representative versions of the invention, and other variants of the described methods and devices with the same principle are within the scope of this invention. For example, the signal samples can be converted to different sets of symbols (not limited to 5 symbols) by using multiple thresholds. Also, the symbolic dynamics can be coded by grouping multiple symbols (e.g., by coding three adjacent symbols instead of two adjacent symbols).

It will be apparent to those skilled in the field that numerous modifications and variations of the described versions of the invention are possible in light of the foregoing discussion. The described versions are presented for purposes of illustration only, and alternate versions of the invention may include some or all of the features described herein. The invention encompasses all such modifications and alternate versions that are defined by, or equivalent to, the invention(s) described by the claims below.

What is claimed is:

1. A method for determination of noise in a sampled physiological signal, the sampled physiological signal including a consecutive sequence of samples, each sample having a signal amplitude, the method including the steps of:
   a. providing a signal quality check window that includes a number of consecutive samples;
   b. providing an upper noise threshold and a lower noise threshold, wherein the upper noise threshold and the lower noise threshold define at least three amplitude ranges:
      (1) a high range for signal amplitudes exceeding the upper noise threshold,
      (2) a medium range for signal amplitudes between the upper noise threshold and the lower noise threshold, and
      (3) a low range for signal amplitudes below the lower noise threshold;
   c. comparing each sample within the quality check window with the upper noise threshold and with the lower noise threshold;
   d. determining any changes between amplitude ranges between each two adjacent sample pairs within the quality check window;
   e. determining a supra-threshold sample sum corresponding to the number of samples outside the medium range; and
   f. generating a low signal quality indication signal if the supra-threshold sample sum exceeds a predefined threshold.

2. The method of claim 1 further including the step of determining threshold crossing counts for each two adjacent signal samples within the quality check window, each threshold crossing count corresponding to the number of thresholds between the adjacent signal samples.

3. The method of claim 2 further including the step of determining a noise threshold crossing sum corresponding to the sum of the threshold crossing counts for the quality check window.

4. The method of claim 3 further including the step of generating a low signal quality indication signal if the noise threshold crossing sum exceeds a predefined threshold.

5. The method of claim 2 further including determining a noise threshold crossing sum wherein:
   a. sums of the threshold crossing counts are determined within separate signal amplitude ranges within the quality check window,
   b. the noise threshold crossing sum corresponds to a weighted sum of the threshold crossing counts, with a predetermined weight being applied to each of sums of the threshold crossing counts occurring within the separate signal amplitude ranges, wherein at least two of the separate signal amplitude ranges have different weights.

6. The method of claim 5 wherein the noise threshold crossing sum defines a complexity index, the method further including the steps of:
   a. comparing the complexity index with a predefined complexity index threshold, and
   b. generating a low signal quality indication signal if the complexity index exceeds the complexity index threshold.

7. The method of claim 5 further including:
   a. detecting an ECG beat at each sample having a signal amplitude exceeding a beat detection threshold;
   b. treating as unreliable the ECG beats immediately before and immediately after a sample for which a low signal quality indication signal was generated.

8. The method of claim 2 further including determining a noise threshold crossing sum wherein separate sums of the threshold crossing counts are determined within separate signal amplitude ranges within the quality check window.

9. The method of claim 1:
   a. further including the step of detecting an ECG beat at one or more samples having a signal amplitude exceeding a beat detection threshold,
   b. wherein the upper noise threshold and/or the lower noise threshold are recalculated after the ECG beat detection.

10. The method of claim 1 further including the steps of:
    a. detecting an ECG beat at a sample having a signal amplitude exceeding a beat detection threshold;
    b. defining a peak detection window around the ECG beat, the peak detection window including one or more samples adjacent to the ECG beat;
    c. determining a peak value corresponding to the maximum absolute amplitude of all of the samples in the peak detection window.

11. The method of claim 10 wherein at least one of the upper and lower noise thresholds is recalculated after the ECG beat, with the recalculated upper and/or lower noise threshold being at least partially dependent on the peak value.

12. The method of claim 10 wherein at least one of the upper and lower noise thresholds is recalculated after the ECG beat, with the recalculated upper and/or lower noise threshold being at least partially dependent on the amplitudes of:
    a. the ECG beat, and
    b. one or more prior ECG beats.

13. The method of claim 10 wherein the upper noise threshold is recalculated after the ECG beat, the method including the steps of:
    a. determining a minimum value (NEW_PEAK) corresponding to the lesser of:
       (1) the peak value (PEAK) of the ECG beat, and
       (2) a weighted average value (OLD_PEAK) of one or more prior peak values from one or more prior ECG beats, the weighted average value (OLD_PEAK) being scaled by a first predefined scaling factor (p) larger than one, b. calculating a weighted average value of:
   (1) the minimum value (NEW_PEAK) determined in step a., and
   (2) the average value (OLD_PEAK) of one or more prior peak values from one or more prior ECG beats,
   the minimum value (NEW_PEAK) and the average value (OLD_PEAK) each being weighted by respective predefined weighting factors (c1, c2) which sum to one, and c. defining the upper noise threshold (NZTHRESH) as the maximum of:
   (1) a predefined minimum noise threshold value (MIN_NZTHRESH), and
   (2) the weighted average value calculated in step b. scaled by a second predefined scaling factor (f), the second predefined scaling factor (f) being larger than zero and smaller than one.

14. The method of claim 1 wherein the physiological signal is an electrocardiogram (ECG) signal or an intracardiac electrogram signal.

15. A medical device including:
   a. one or more physiological signal sensors, and
   b. a processor configured to perform the steps of claim 1.

16. A method for determination of noise in a sampled physiological signal, the sampled physiological signal including a consecutive sequence of samples, each sample having a signal amplitude, the method including the steps of:
   a. providing a signal quality check window that includes a number of consecutive samples;
   b. providing:
      (1) an upper noise threshold at a signal amplitude greater than the average signal amplitude of the samples, and
      (2) a lower noise threshold at a signal amplitude less than the average signal amplitude of the samples,
      with a noise tolerance zone being defined between the upper and lower noise thresholds;
   c. identifying one or more of the samples outside the noise tolerance zone as having low signal quality;
   d. detecting an ECG beat at one or more samples having a signal amplitude exceeding a beat detection threshold,
   e. following the ECG beat, adjusting one or more of the upper and lower noise thresholds in dependence on the amplitudes of the ECG beat and one or more prior ECG beats.

17. The method of claim 16 further including the steps of:
   a. determining a supra-threshold sample sum corresponding to the number of samples in the quality check window having an amplitude that either:
      (1) exceeds the upper noise threshold, or
      (2) falls below the lower noise threshold,
   b. indicating a low signal quality for at least one of the samples within the quality check window if the supra-threshold sample sum exceeds a predefined value.

18. The method of claim 16 further including the steps of:
   a. determining a noise threshold crossing sum corresponding to the sum of the number of noise threshold crossings between each two consecutive samples in the quality check window,
   b. indicating a low signal quality for at least one of the samples within the quality check window if the noise threshold crossing sum exceeds a predefined value.

19. The method of claim 16 wherein the step of adjusting one or more of the upper and lower noise thresholds following the ECG beat includes:

a. determining a minimum value of:
   (1) the peak amplitude of the ECG beat, and
   (2) an average value representative of the peak amplitudes of one or more prior ECG beats,
b. calculating a weighted average value of:
   (1) the minimum value determined in step a., and
   (2) an average value representative of the peak amplitudes of one or more prior ECG beats, and
c. adjusting one or more of the upper and lower noise thresholds to have a magnitude dependent on:
   (1) a predefined minimum noise threshold value), and
   (2) the weighted average value calculated in step b.

20. The method of claim 16 further including determining a noise threshold crossing sum wherein:
   a. sums of the threshold crossing counts are determined within separate signal amplitude ranges within the quality check window,
   b. the noise threshold crossing sum corresponds to a weighted sum of the threshold crossing counts, with a predetermined weight being applied to each of sums of the threshold crossing counts occurring within the separate signal amplitude ranges, wherein at least two of the separate signal amplitude ranges have different weights.

21. A method for determination of noise in a sampled physiological signal, the sampled physiological signal including a consecutive sequence of samples, each sample having a signal amplitude, the method including the steps of
   a. defining a quality check window including a number (NZDW) of samples,
   b. determining a supra-threshold sample sum (STS_SUM) corresponding to the number of samples in the quality check window having an amplitude that either:
      (1) exceeds an upper noise threshold (NZTHRESH), or
      (2) falls below a lower noise threshold (−NZTHRESH),
   c. determining a noise threshold crossing sum (NZX_SUM) corresponding to the sum of the number of noise threshold crossings between each two consecutive samples in the quality check window,
   d. indicating a low signal quality for at least one of the samples within the quality check window if:
      (1) the noise threshold crossing sum (NZX_SUM) exceeds a first predefined value (TX1), or
      (2) the supra-threshold sample sum (STS_SUM) exceeds a second predefined value (ST1).

22. The method of claim 21 wherein a low signal quality is also indicated if:
   a. the noise threshold crossing sum (NZX_SUM) exceeds a third predefined value (TX2), and
   b. the supra-threshold sample sum (STS_SUM) exceeds a fourth predefined value (ST2).

23. The method of claim 21:
   a. further including the step of detecting an ECG beat at one or more samples having a signal amplitude exceeding a beat detection threshold,
   b. wherein at least one of:
      (1) the upper noise threshold (NZTHRESH), and
      (2) the lower noise threshold (−NZTHRESH),
      are adjusted after the ECG beat detection.

24. The method of claim 23 wherein at least one of the upper noise threshold (NZTHRESH) and the lower noise threshold (−NZTHRESH) are adjusted at least partially in dependence on the amplitudes of:
   a. the ECG beat, and
   b. one or more prior ECG beats.

25. The method of claim 21 wherein the noise threshold crossing sum (NZX_SUM) corresponds to the weighted sum of:

a. a first sum representing the number of noise threshold crossings within a first signal amplitude range, and
b. a second sum representing the number of noise threshold crossings within a second signal amplitude range, the second signal amplitude range having greater amplitudes than the first amplitude range,
wherein different weights are applied to the first and second sums.

* * * * *